(12) United States Patent
Potter et al.

(10) Patent No.: US 7,985,232 B2
(45) Date of Patent: Jul. 26, 2011

(54) DETACHABLE HEMOSTASIS VALVE AND SPLITTABLE SHEATH ASSEMBLY

(75) Inventors: Daniel J. Potter, Stillwater, MN (US); Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1533 days.

(21) Appl. No.: 10/873,705

(22) Filed: Jun. 21, 2004

(65) Prior Publication Data
US 2005/0010238 A1 Jan. 13, 2005

Related U.S. Application Data

(60) Provisional application No. 60/485,783, filed on Jul. 8, 2003.

(51) Int. Cl.
*A61B 19/00* (2006.01)
*A61M 5/178* (2006.01)

(52) U.S. Cl. .......................... 606/129; 604/160

(58) Field of Classification Search ................ 604/236, 604/237, 244, 246–250, 533–539, 129, 523, 604/160; 24/455; 606/129
See application file for complete search history.

(56) References Cited

U.S. PATENT DOCUMENTS

| | | | |
|---|---|---|---|
| 4,909,798 A | 3/1990 | Fleischhacker et al. | |
| 5,114,408 A | 5/1992 | Fleischhaker et al. | |
| 5,250,033 A | 10/1993 | Evans | |
| 5,312,355 A * | 5/1994 | Lee | 604/160 |
| 5,352,215 A * | 10/1994 | Thome et al. | 604/284 |
| 5,423,762 A * | 6/1995 | Hillstead | 604/167 |
| 5,456,673 A * | 10/1995 | Ziegler et al. | 604/264 |
| 5,685,858 A * | 11/1997 | Kawand | 604/171 |
| 5,843,031 A | 12/1998 | Hermann et al. | |
| 5,911,710 A * | 6/1999 | Barry | 604/249 |
| 5,927,277 A * | 7/1999 | Baudino et al. | 600/386 |
| 6,083,207 A * | 7/2000 | Heck | 604/256 |
| 6,142,981 A | 11/2000 | Heck et al. | |
| 6,203,321 B1 * | 3/2001 | Helmer et al. | 433/95 |
| 6,423,053 B1 * | 7/2002 | Lee | 604/533 |
| 6,632,200 B2 | 10/2003 | Guo et al. | |

(Continued)

FOREIGN PATENT DOCUMENTS
EP 0631793 A 1/1995
(Continued)

OTHER PUBLICATIONS
International Communication and Supplementary European Search Report dated Aug. 7, 2008.

*Primary Examiner* — John M. Brittingham
*Assistant Examiner* — Michael J Anderson
(74) *Attorney, Agent, or Firm* — Heimbecher & Assoc., LLC

(57) ABSTRACT

A system for connecting a hemostasis valve to a splittable sheath includes an interface formed between a ledge on the proximal end of a cannula portion of the hemostasis valve and an engagement structure aligned with the handles of the splittable sheath. Pulling the handles to split the sheath likewise disengages the ledge from the engagement structure. A snap ring on the cannula portion engages a snap ring in the lumen of a sheath hub formed on the proximal end of the splittable sheath. An O-ring between the cannula portion and the sheath hub provides a fluid-tight seal.

21 Claims, 24 Drawing Sheets

U.S. PATENT DOCUMENTS

| | | | |
|---|---|---|---|
| 6,712,791 B2 * | 3/2004 | Lui et al. | 604/167.04 |
| 6,808,509 B1 * | 10/2004 | Davey | 604/167.04 |
| 6,969,381 B2 * | 11/2005 | Voorhees | 604/534 |
| 7,101,353 B2 * | 9/2006 | Lui et al. | 604/167.06 |
| 7,303,552 B1 * | 12/2007 | Chu et al. | 604/263 |
| 2003/0050604 A1 * | 3/2003 | Lui et al. | 604/167.06 |
| 2004/0254534 A1 * | 12/2004 | Bjorkman et al. | 604/160 |
| 2004/0260243 A1 * | 12/2004 | Rickerd | 604/161 |
| 2008/0071221 A1 * | 3/2008 | Rickerd | 604/161 |

FOREIGN PATENT DOCUMENTS

| | | |
|---|---|---|
| WO | 0149363 A | 12/2001 |

* cited by examiner

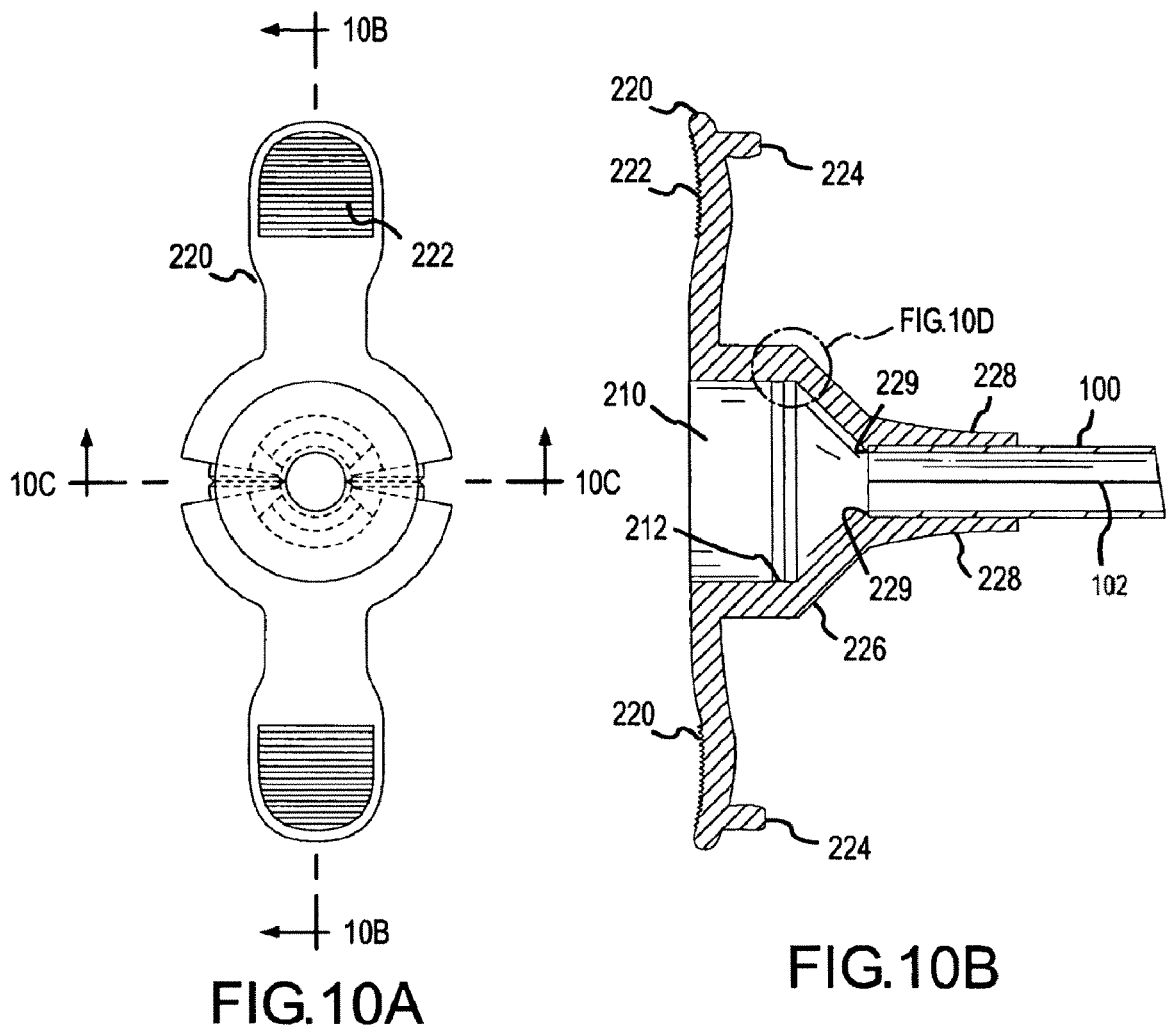
FIG.10A
FIG.10B
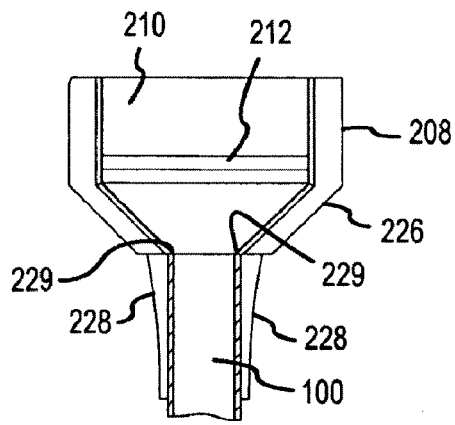
FIG.10C
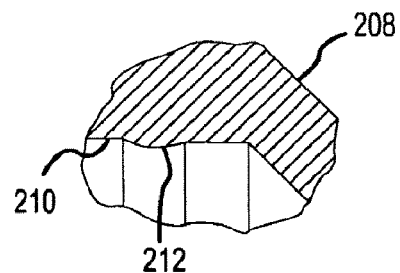
FIG.10D

DETACHABLE HEMOSTASIS VALVE AND SPLITTABLE SHEATH ASSEMBLY

CROSS-REFERENCE TO RELATED APPLICATIONS

This application claims priority pursuant to 35 §U.S.C. 119(e) to U.S. provisional application No. 60/485,783, filed 8 Jul. 2003, entitled Detachable Hemostasis Valve and Splittable Sheath Assembly, which is hereby incorporated by reference in its entirety as though fully set forth herein.

BACKGROUND OF INVENTION a. Field of the Invention

This invention relates generally to the field of medical instruments used for intra-arterial and intravenous introduction of instruments and more specifically to a connection assembly for creating a fluid seal connection between such medical instruments.

b. Background Art

There are a number of medical procedures which require the introduction of medical instruments into arteries and veins. In one such procedure, known as the Seldinger procedure, a surgical opening is made in a vein or artery with a needle. A guide wire is then inserted through the lumen of the needle into the vein or artery. The needle is withdrawn, leaving the guide wire in place. A dilator is then inserted over the guide wire inside an associated sheath. The dilator is used to increase the size of the needle opening in the vessel in order to introduce larger diameter instruments. The dilator and guidewire are removed once the sheath is in place. At this point, various types of catheters or leads may be inserted into the vessel within the lumen of the sheath using the sheath as a conduit to prevent damage to the vessel wall.

In certain medical procedures, for example, where a pacemaker lead is inserted into a patient, a sheath is normally used to guide the pacemaker lead to the appropriate location. Before the pacemaker lead is permanently secured in place and attached to a pacemaker, the sheath must be removed. Because of the size of its lumen, the sheath cannot simply slip over the exterior end of the pacemaker lead as that end of the lead contains a connector coupling for connection to the pacemaker.

Accordingly, there have been disclosed a number of splittable sheaths for use in the introduction of pacemaker lead. These sheaths can be split in half while still surrounding the pacemaker lead. In this use, once the pacemaker lead is in place, the sheath is longitudinally severed and removed from the pacemaker lead. For example, U.S. Pat. No. 4,983,168 discloses such a layered, peel-away hollow sheath, wherein the sheath wall is comprised of at least two layers, an inside cylindrical layer and an outside layer of two semi-cylindrical segments defining opposed, axially-directed slits or slots therebetween. The slits function as tear lines. U.S. Pat. No. 4,596,559 discloses a tear away sheath for use with a disposable introducer set in conjunction with a catheter. U.S. Pat. Nos. Re. 31,855 and 4,581,025 disclose a sheath that has an internal molecular orientation which tears easily in a lengthwise direction and with great difficulty in a crosswise or oblique direction. Longitudinally scored or perforated sheaths are also disclosed in U.S. Pat. Nos. 4,166,469; 4,243,050; 4,345,606; and 4,451,256.

Several problems may be encountered during the use of these splittable sheaths. For example, during the introduction of a pacemaker lead, a significant amount of bleeding may occur at the operation site, depending upon the blood pressure present in the vessel. Once the sheath is in place within a vessel, it provides a passageway for the free flow of blood away from the operation site. Further, because of this flow of blood, clotting may occur if the sheath remains in position for an extended period of time. These clots may cause emboli which may pass to the lungs with a negative impact on the patient. The use of sheaths may also provide a passageway for the introduction of air into the vessel. The inadvertent introduction of air into the blood system can cause air emboli, also potentially negatively affecting the patient. Because of such problems, splittable sheaths are often removed from the theater of operation as soon as possible, even if it would be preferable to maintain them in position for a longer period of time. Such hurried procedures can result in errors or medical complications.

One simple method for restricting the flow of blood out of a sheath while a pacemaker lead is introduced is for the physician to place a thumb over the exposed end of the sheath or to squeeze or pinch the exposed end of the sheath between the thumb and forefinger. However, neither of these methods for reducing the undesired flow of blood and air through the sheath is desirable, because the opportunity for loss of blood and introduction of air is still present. In addition, the structure of such a sheath still requires the surgeon to hold onto it while it is in place in the vessel, thereby limiting the surgeon's ability to perform other medical procedures at the same time. Moreover, squeezing the exposed end of the sheath can deform or possibly break the sheath, making lead insertion difficult and increasing the likelihood of damage to the lead as it passes through the sheath. Further, even when holding the end of the sheath or pinching the sheath, the flow of blood out of the sheath is not entirely arrested.

For these reasons, a hemostasis valve is often used in conjunction with a sheath to limit blood flow during the introduction of guide wires, catheters, pacemaker leads and other similar medical devices into the heart. This use of a hemostasis valve may, however, become a cause for concern. For example, because the exterior end of a pacemaker lead is often larger than the opening in conventional hemostasis valves, it is not possible for pacemaker leads to pass through these conventional hemostasis valves. In many cases the hemostasis valve is designed for use with a specific size of a catheter. Such hemostasis valves have been disclosed, for example, in U.S. Pat. Nos. 5,092,857 and 4,909,798. Another solution to this problem has been to provide splittable hemostasis valves integrally formed with splittable sheaths for the introduction of pacemaker leads as disclosed, for example, in U.S. Pat. Nos. 5,312,355 and 5,125,904. Similarly, splittable hemostasis valves that are not integral with a sheath, but merely connected thereto, may be used, for example, as disclosed in U.S. Pat. No. 6,083,207. A further solution to the problem has been to provide a "universal" hemostasis valve, wherein the valve assembly is designed to accommodate leads and catheters of a wide range of diameters.

A wide variety of circumstances can dictate which type of hemostasis valve is chosen for a particular application or in a particular situation. For example, the physician may want to delay introduction of a hemostasis valve onto a sheath until after the sheath is in position. This would suggest that an integral hemostasis valve and sheath is not desirable. In some circumstances, multiple leads or catheters of various diameters may need to be used. In these instances, particularly sized hemostasis valves would not be preferred. In other circumstances, the hemostasis valve may need to be removed during the operation, or perhaps removed and replaced several different times while the sheath remains in place. Such use might counsel against a splittable hemostasis valve that may be prone to leakage once split. Further, it is sometimes necessary to remove the hemostasis valve from the operating theater at a time when the sheath is still in use.

When the particular choice is made to use a non-splitting hemostasis valve, a further problem may arise that remains unaddressed by prior designs. Once introduced into the body intravascularly, leads are often placed in particular and sensitive positions and the intention is for the lead to remain in place. This is particularly true in the case of pacemaker leads that are imbedded in precise locations in the heart muscle to achieve particular results. The problem suggested occurs when attempting to remove a hemostasis valve from the lead. Sometimes the hemostasis valve is attached to the sheath with a Luer lock interface. When unscrewing the hemostasis valve, the friction fit between the valve assembly and the lead can cause the lead to rotate and either dislodge from or otherwise become misplaced about the heart muscle. Even when other fittings are used, the friction fit between the hemostasis valve and the lead can cause the lead to become dislodged from the heart muscle when removing the hemostasis valve.

The information included in this Background section of the specification, including any references cited herein and any description or discussion thereof, is included for technical reference purposes only, but is not to be regarded as subject matter by which the scope of the invention is to be bound.

SUMMARY OF THE INVENTION

The invention disclosed herein is directed to a hemostasis device and splittable sheath assembly designed for both attachment with and detachment from each other in a manner designed to reduce any force exerted on an indwelling lead. Common among the several embodiments of the invention is the ability to disconnect the splittable sheath from the hemostasis device by merely splitting the sheath. No prior removal of the connection between the hemostasis device and the splittable sheath is required. The action of splitting the sheath simultaneously uncouples the splittable sheath from the hemostasis device.

Generally, the invention is directed to a connection system for connecting a hemostasis valve with a splittable sheath. The system includes a first coupler disposed on a cannula portion of the hemostasis valve, and a bifurcated sheath hub formed of opposing lateral halves joined with a proximal end of the splittable sheath. The bifurcated sheath hub further has a second coupler disposed thereon. The first coupler engages the second coupler to couple the hemostasis valve with the splittable sheath. The second coupler disengages from the first coupler when the opposing lateral halves of the bifurcated sheath hub are separated from each other to split the splittable sheath. The bifurcated sheath hub may further have a pair of handles, wherein each handle is positioned on one of the opposing lateral halves of the bifurcated sheath hub, respectively. The bifurcated sheath hub may also have a pair of tabs, each extending distally from one of the opposing lateral halves of the bifurcated sheath hub and adhered to an outer wall of the splittable sheath. In an alternate arrangement, the pair of handles may be joined with the bifurcated sheath hub, wherein each handle is positioned on one of the tabs, respectively.

The hemostasis valve may further have a first connector disposed on the cannula portion thereof and the bifurcated sheath hub may further have a second connector disposed thereon. The first connector engages the second connector to axially connect the hemostasis valve with the splittable sheath. The second connector disengages from the first connector when the opposing lateral halves of the bifurcated sheath hub are separated from each other to split the splittable sheath.

The hemostasis valve may also have an O-ring disposed about the cannula portion, the O-ring of slightly larger diameter than the lumen of the bifurcated sheath hub defined by the interior surface of the annular wall of the bifurcated sheath hub. The O-ring helps create a fluid-tight seal with the bifurcated sheath hub when the cannula portion is seated within the lumen.

In one embodiment the first coupler may be a first snap ring disposed about a distal end of the cannula portion, wherein the first snap ring is of slightly larger diameter than the interior surface of the annular wall of the sheath hub. The second coupler may likewise be a second snap ring formed on the interior surface of the annular wall, wherein the second snap ring is of slightly smaller diameter than the diameter of the interior surface of the annular wall adjacent the second snap ring. When the hemostasis valve is coupled with the splittable sheath, the first snap ring is positioned distal and adjacent to the second snap ring.

In another embodiment, the first coupler may be a pair of clips joined with the bifurcated sheath hub. Each clip defines a lip and a recess and is positioned on and extends proximally from a proximal end of one of the opposing lateral halves of the bifurcated sheath hub, respectively. The second coupler may be a pair of ledges disposed on opposing sides of the cannula portion. When the hemostasis valve is coupled with the splittable sheath, each ledge is retained within one of the recesses by one of the lips, respectively.

In a further embodiment, the first coupler may alternatively be two sets of paired tabs. Each tab may form a portion of the annular wall of the bifurcated sheath hub and be positioned on the proximal end of the bifurcated sheath hub with the sets of paired tabs positioned opposite each other. Further, each tab in each pair of tabs is positioned apart from the other on one of the opposing lateral halves of the bifurcated sheath hub, respectively. Each tab may further have a tooth on its proximal end extending radially into the lumen. The second coupler may have a circumferential groove about the cannula portion. When the hemostasis valve is coupled with the splittable sheath, each tooth in each of the tabs is retained within the circumferential groove.

In yet another embodiment, the first coupler may be formed of four clips, each with a lip and a recess, joined with the bifurcated sheath hub. Each clip is positioned on and extends proximally from a proximal end of the bifurcated sheath hub and is spaced equidistant from each adjacent clip circumferentially about the lumen. Pairs of the four clips are positioned on one of the opposing lateral halves, respectively. The second coupler may have four ledges disposed equidistant from each adjacent ledge circumferentially about the cannula portion. When the hemostasis valve is coupled with the splittable sheath, each ledge is retained within one of the recesses by one of the lips, respectively.

In another embodiment, the first coupler may have at least one tab positioned on the proximal end of the bifurcated sheath hub. The at least one tab forms a portion of the annular wall of the bifurcated sheath hub and is joined with the bifurcated sheath hub via a structural hinge. The at least one tab further comprises a tooth extending radially into the lumen. The second coupler may be a circumferential groove about the cannula portion. When the hemostasis valve is coupled with the splittable sheath, the tooth is retained within the circumferential groove.

In a further embodiment of the invention, the first coupler comprises a nut retained about the cannula portion. The nut may be formed with a pair of ledges disposed on opposing sides of an outer surface of the nut. The second coupler may be a pair of clips joined with the bifurcated sheath hub. Each clip defines a lip and a recess and is positioned on and extends proximally from a proximal end of one of the opposing lateral halves of the bifurcated sheath hub, respectively. When the hemostasis valve is coupled with the splittable sheath, each ledge is retained within one of the recesses by one of the lips, respectively.

In an alternative embodiment of the invention, a connection system for connecting a hemostasis valve with a splittable sheath is disclosed. The system is composed of a sheath hub connected with a proximal end of the splittable sheath, and a pair of handles connected with the sheath hub, each handle positioned on an opposing lateral side of the sheath hub. The hemostasis valve has a cannula portion extending distally therefrom, a first snap ring disposed on a distal end of the cannula portion, and a first engagement structure disposed on the cannula portion proximal to the first snap ring. The sheath hub has an annular wall defining a lumen, a second snap ring formed on an interior surface of the annular wall, and a second engagement structure disposed on a proximal end thereof. When the hemostasis valve is connected with the splittable sheath, the cannula portion seats within the lumen of the sheath hub, the first snap ring engages the second snap ring, and the first engagement structure couples with the second engagement structure.

In yet another embodiment of the invention, a system for connecting a hemostasis valve and a sheath is disclosed. The hemostasis valve has an outer surface, a first coupling interface disposed circumferentially on a distal end of the outer surface, an O-ring disposed circumferentially on the outer surface proximal to the first coupling interface. The sheath is predisposed in construction to longitudinally split into separate first and second halves. An inner wall surface of the sheath defines a generally cylindrical lumen, and the inner wall surface further defines a second coupling interface disposed circumferentially about the inner wall surface. A first handle and a second handle are each connected with an outer wall surface of the sheath. The first handle is positioned on the first half of the sheath and the second handle is positioned on the second half of the sheath. Both the first and second handles are positioned at a proximal end of the sheath. When the hemostasis valve is connected with the sheath, the first coupling interface engages the second coupling interface and the O-ring frictionally engages the inner wall surface of the sheath. When an outward radial and distal force is exerted on each of the first and second handles, the sheath separates longitudinally into the first and second halves and the second coupling interface disengages from the first coupling interface.

An alternative embodiment of the invention is directed to a splittable sheath for joining with a hemostasis valve with a first snap ring and a first engagement structure. The splittable sheath is composed of a cannula predisposed to separate longitudinally; a bifurcated sheath hub formed of opposing lateral halves joined with a proximal end of the cannula, and a pair of handles connected with the bifurcated sheath hub. Each handle is positioned on an opposing lateral side of the bifurcated sheath hub. The bifurcated sheath hub includes an annular wall defining a lumen, a second snap ring formed on an interior surface of the annular wall, and a second engagement structure disposed on a proximal end thereof. When the splittable sheath is connected with the hemostasis valve, the second snap engages ring the first snap ring and the second engagement structure couples with the first engagement structure. When an outward radial and distal force is exerted on the handles, the bifurcated sheath hub and cannula each separate longitudinally, the second engagement structure disengages from the first engagement structure, and the second snap ring disengages from the first snap ring.

Other features, utilities and advantages of various embodiments of the invention will be apparent from the following more particular description of embodiments of the invention as illustrated in the accompanying drawings and defined in the appended claims.

BRIEF DESCRIPTION OF THE DRAWINGS

FIG. 10A is a top plan view of an alternative splittable sheath and sheath hub.

FIG. 10B is a side elevation view in cross-section of the splittable sheath and sheath hub as indicated in FIG. 10A.

FIG. 10C is a side elevation view in cross-section of the splittable sheath and sheath hub as indicated in FIG. 10A.

FIG. 10D is a magnified view of an area of the sheath hub detailing a snap ring as indicated in FIG. 10B.

DETAILED DESCRIPTION OF THE INVENTION

Figure 1:
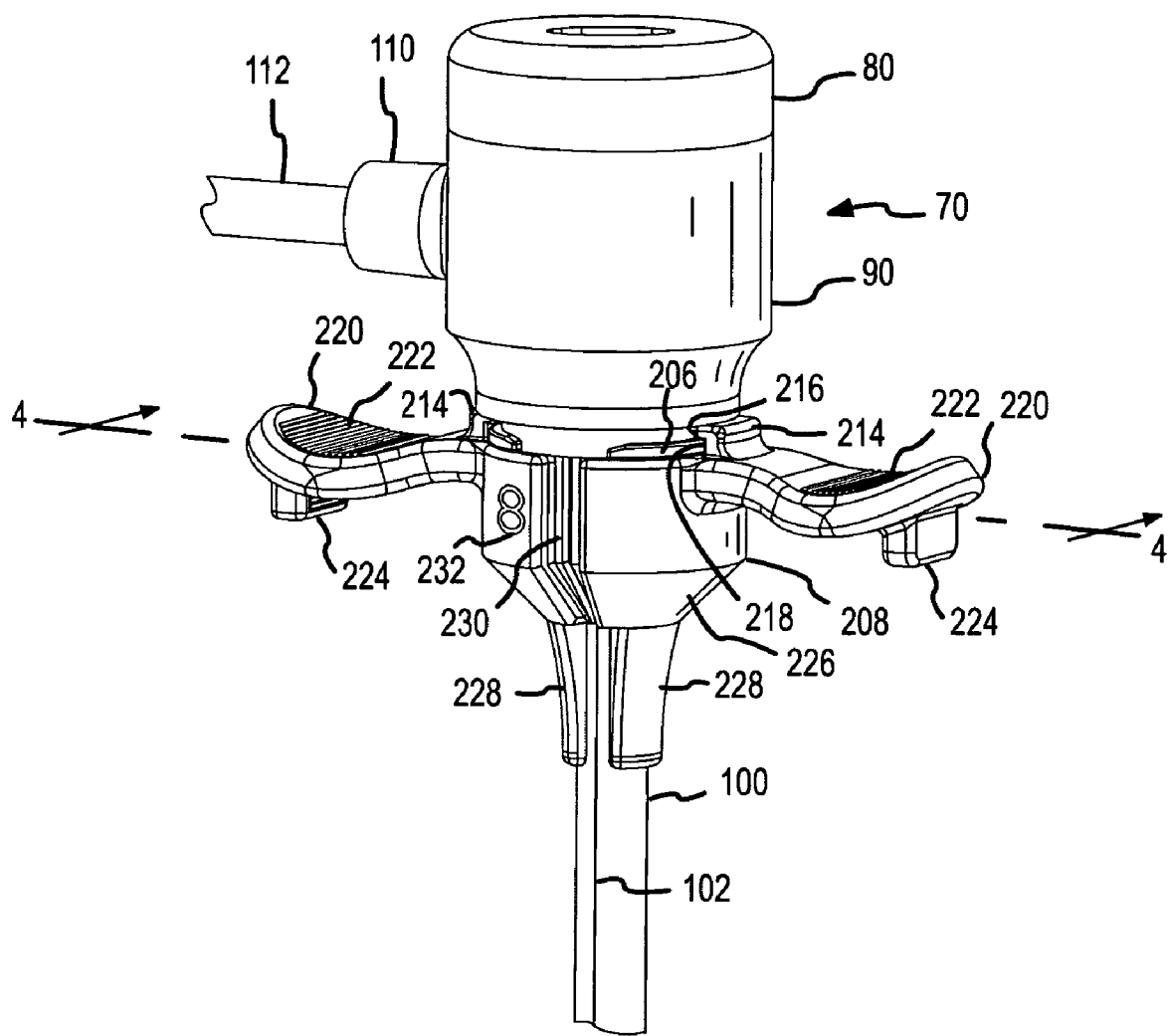
FIG. 1 is an isometric view of a hemostasis device and splittable sheath assembly according to a first embodiment of the invention.
Figure 2:
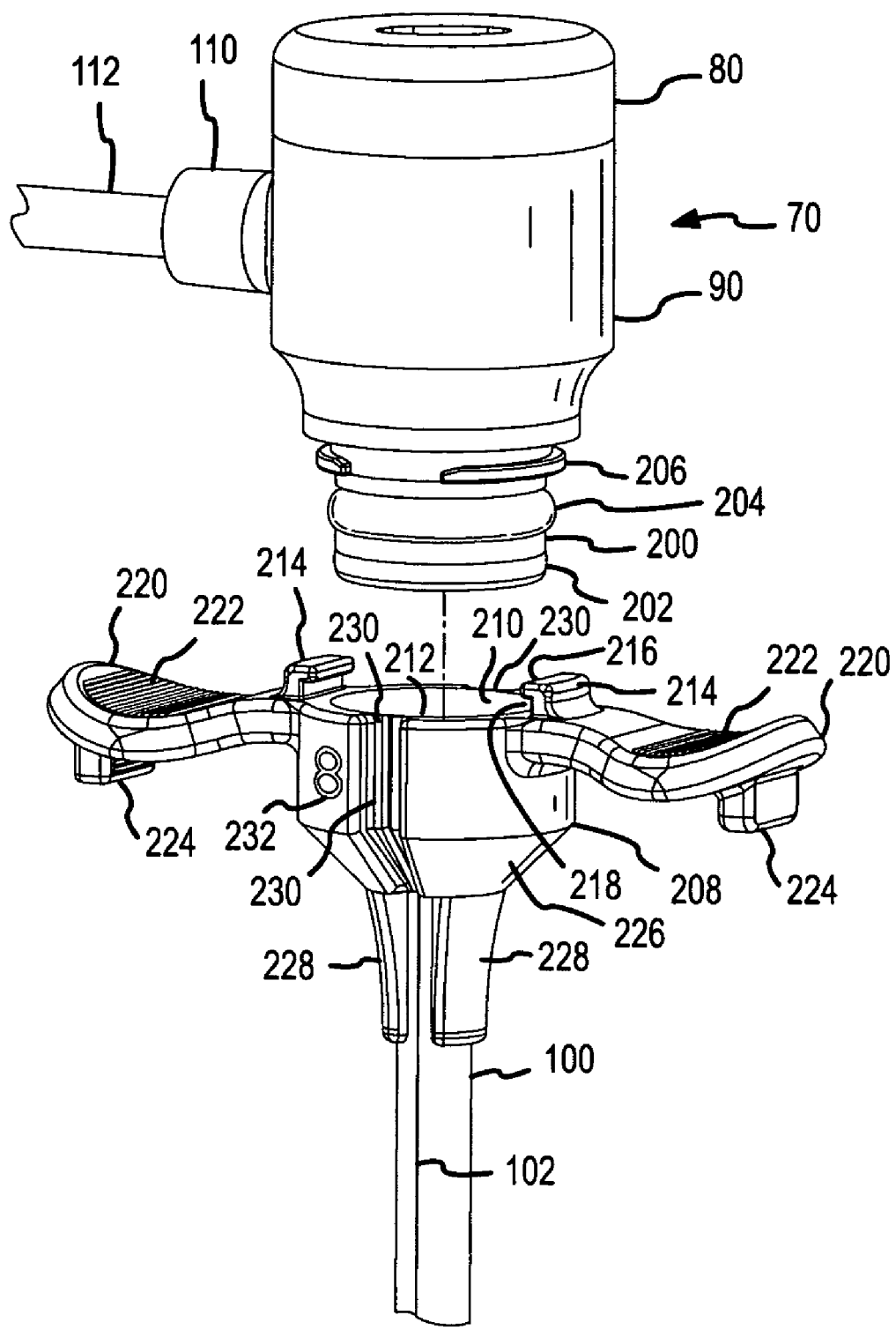
FIG. 2 is an isometric view of the hemostasis device and splittable sheath assembly of FIG. 1 with hemostasis device separate from the splittable sheath.

The following disclosure of the invention describes a hemostasis device and splittable sheath assembly designed for both attachment with and detachment from each other in a manner designed to reduce any force exerted on an indwelling lead. Several embodiments of the invention are disclosed herein. Common among the embodiments of the invention is the ability to disconnect the splittable sheath from the hemostasis device by merely splitting the sheath. No prior removal of the connection between the hemostasis device and the splittable sheath is required. Stated another way, while various structures and methodologies are employed as disclosed herein for attaching the hemostasis device to the splittable sheath, employing the reverse of these methodologies for disconnecting the hemostasis device from the splittable sheath is not required before the sheath is able to be split. The action of splitting the sheath simultaneously uncouples the splittable sheath from the hemostasis device.

A first embodiment of the present inventive coupling system for a hemostasis device 70 and a splittable sheath 100 is depicted initially in FIGS. 1-4. The hemostasis device 70 is formed of four major components. The first of these components is the cap 80, which is attached to the proximal end of the second component—the longitudinally extended valve housing 90. The valve housing 90 has proximal and distal opposing openings through which elongated medical devices are inserted into and out of the interior of the valve housing 90. Hereinafter, the term "lead" will be used to refer generally to all devices and instruments, including guidewires, leads, dilators, and catheters that may be inserted into the hemostasis device 70 and splittable sheath 100. The hemostasis device 70 is provided with a cannula portion 200 extending distally therefrom, which is the third major component. The cannula portion 200 is designed to engage with a sheath hub 208 connected with the proximal end of a splittable sheath 100. The cannula portion 200 may have an annular cannula snap ring 202 toward its distal end and extending from the outer surface of the cannula portion 200 as a small annular bump. An O-ring 204 may be fitted about the outer surface of the cannula portion 200 within an annular recess 205 proximal to the snap ring 202. Other types of fluid-tight seals may likewise be employed, for exampled, a gasket interfacing between the cannula portion 200 and the sheath hub 208.

Figure 3:
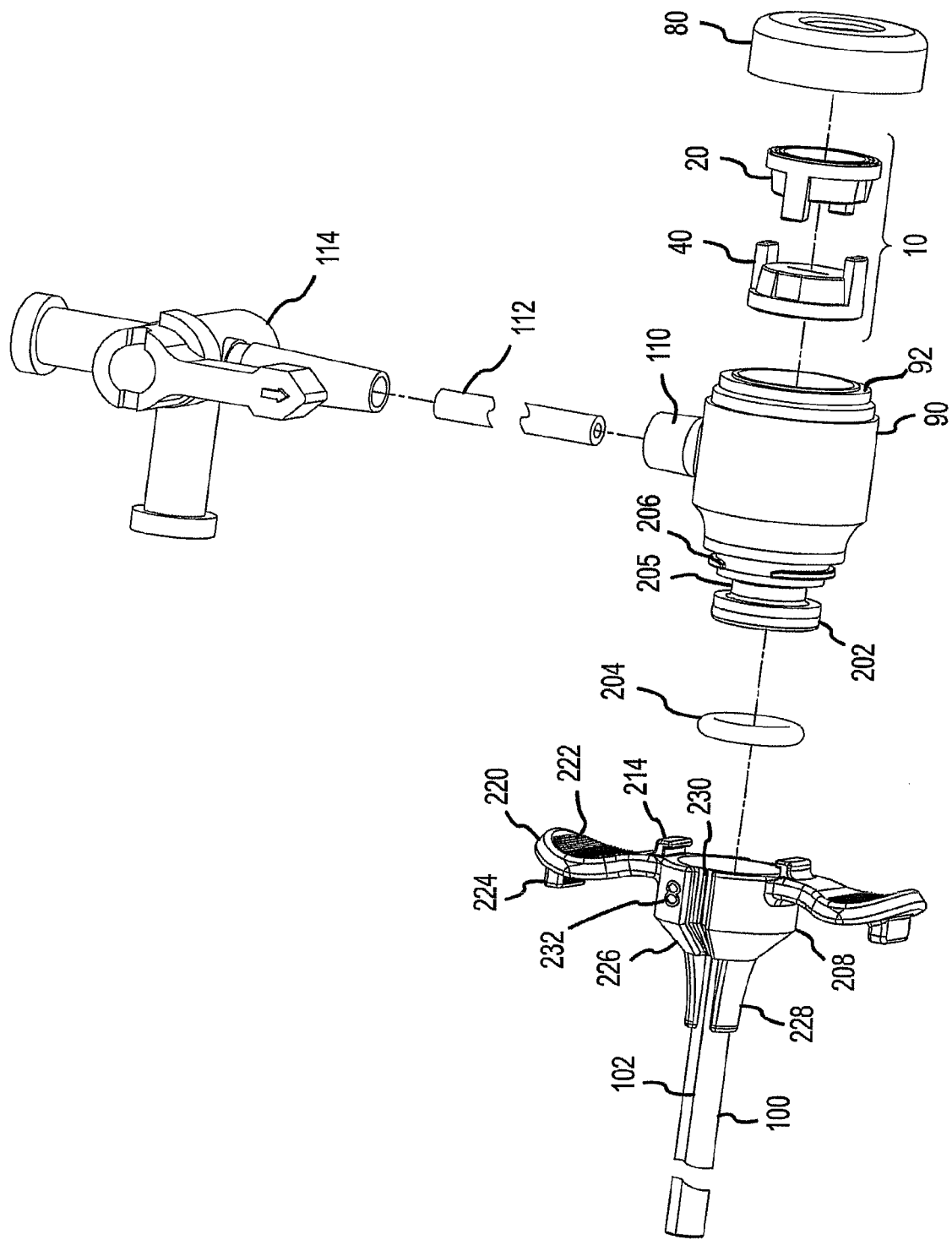
FIG. 3 is an exploded isometric view of the hemostasis device and splittable sheath assembly of FIG. 1.

The cap 80 and the valve housing 90 may be formed from a relatively hard thermoplastic, such as polycarbonate, high-density polyethylene, or an acrylonitrile-butadiene styrene copolymer. The cap 80 may be secured to the valve housing 90, for example, by gluing, heat sealing, ultrasonic bonding, and by mechanically attaching the cap 80 to the valve housing 90, for example, with threads, clips, or a snap fitting. In one embodiment, the cap 80 and the valve housing 90 may be first molded with respective interference fits and then may additionally be ultrasonically welded or bonded together with heat adhesion. A side port 110 is preferably secured to or formed into the valve housing 90 distal to the hemostasis valve 10, as shown in FIGS. 1-4, to provide for the perfusion and aspiration of fluids into and out of the hemostasis device 70. A tube 112 may be inserted in to the side port 110 and connected with a stop cock 114, as shown in FIG. 3, to regulate the introduction of such fluids.

Figure 4:
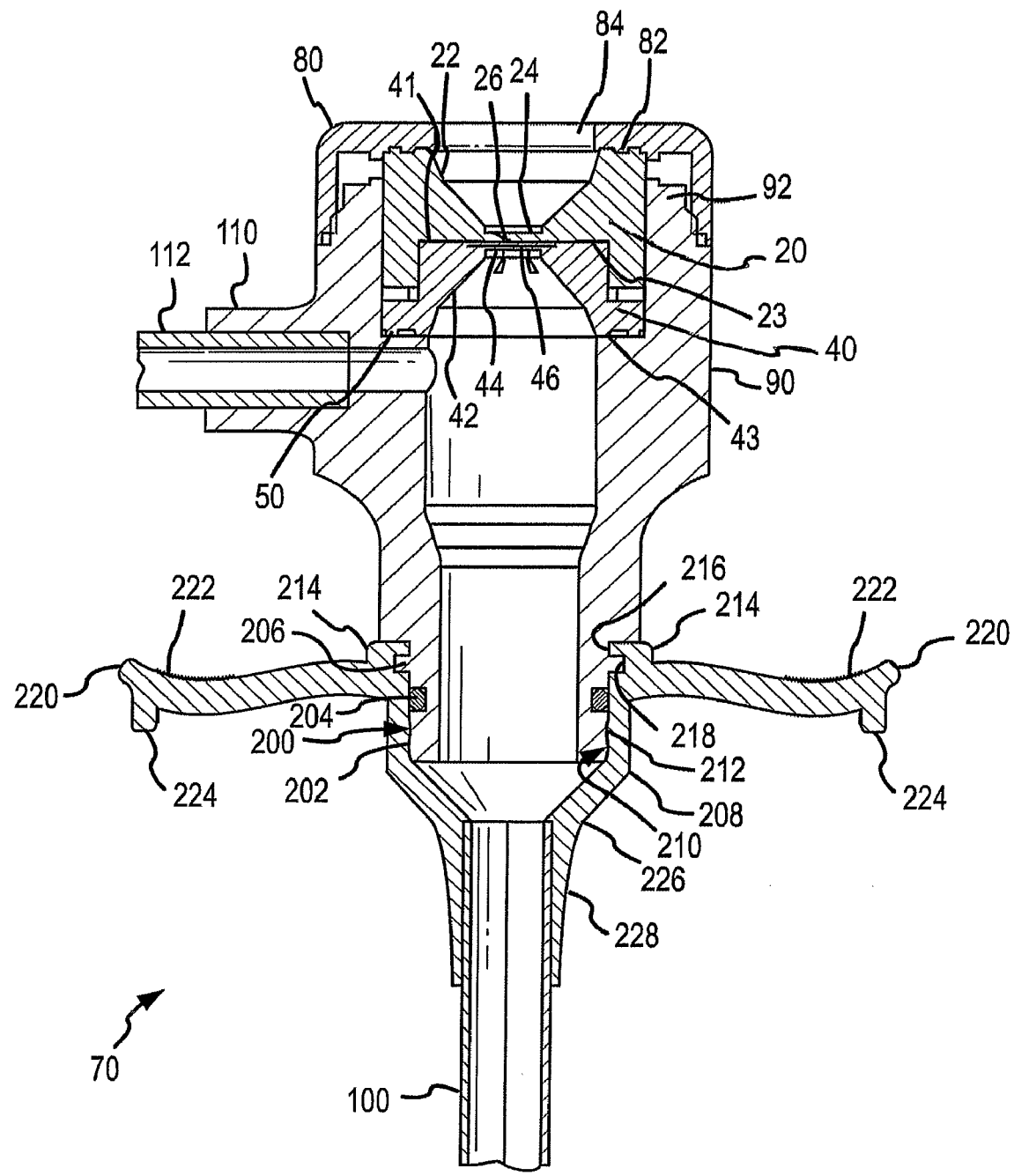
FIG. 4 is an elevation view in cross-section of the hemostasis device and splittable sheath assembly as indicated in FIG. 1.

The fourth major component of the hemostasis device 70 of the present invention is the hemostasis valve 10 and consisting of a proximal valve gasket 20 and a distal valve gasket 40 as shown in FIGS. 3-7C. An entry face 21 of the proximal valve gasket 20 contacts the inner surface of the cap 80 of the hemostasis device 70 and an exit face 23 of the proximal valve gasket 20 contacts an entry face 41 of the distal valve gasket 40, as shown in FIG. 4. An exit face 43 of the distal valve gasket 40 contacts a surface on the interior of the valve housing 90 as shown in FIG. 4 to hold the valve gaskets 20, 40 securely within the valve housing 90. The valve gaskets 20, 40 may be made from a pliant, highly elastic polymeric material, such as a silicone rubber, or a thermoplastic elastomer (e.g., olefinic, styrenic, polyamide-based, polyester-based, or a hydrocarbon rubber, such as polybutadiene, polyisoprene, or natural rubber), which can readily and repeatedly permit passage of elongated leads of varying diameters through the hemostasis valve 10.

Figure 5:
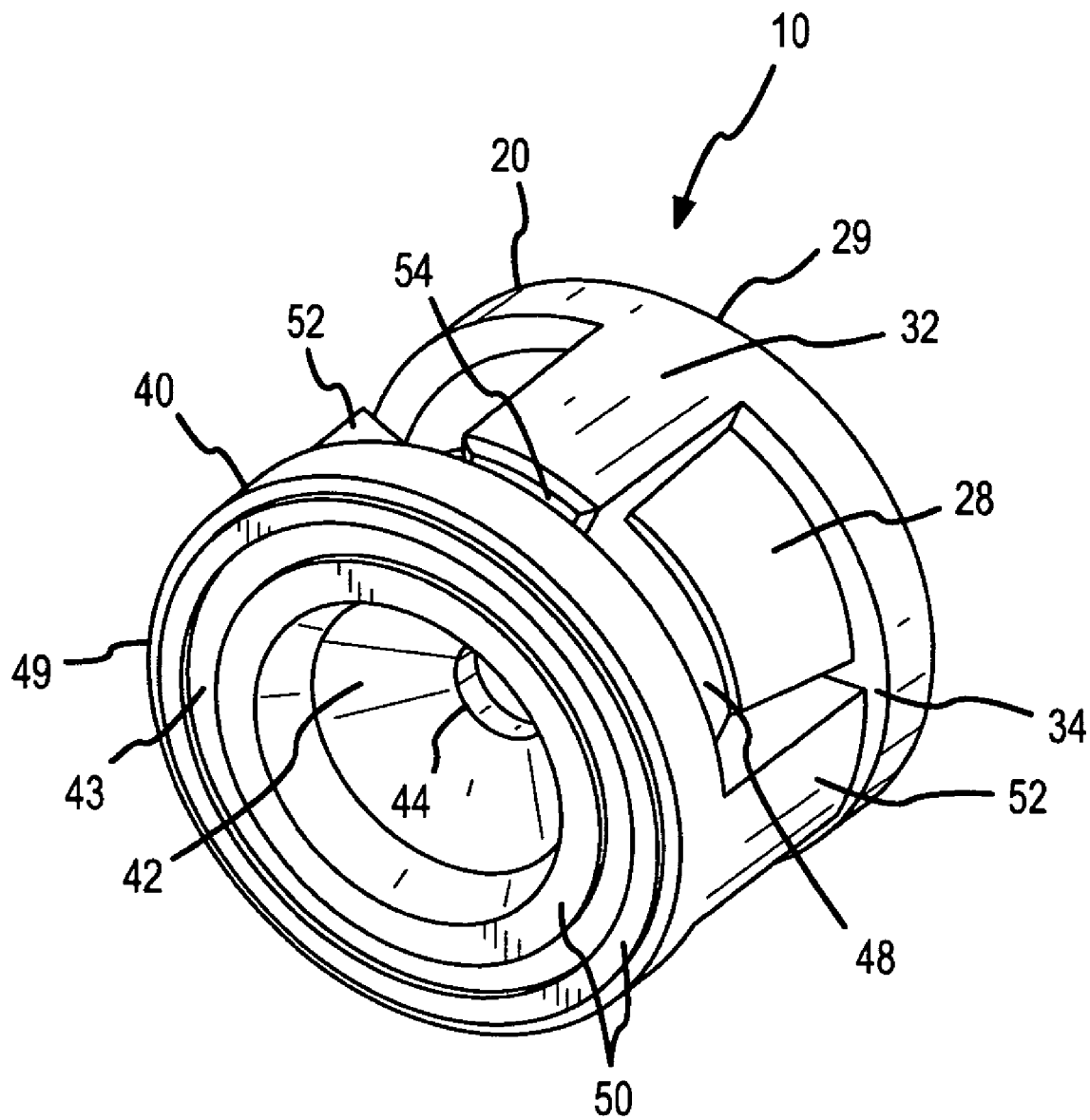
FIG. 5 is an isometric view of the valve gaskets of the hemostasis device of FIG. 1.

The proximal valve gasket 20 and the distal valve gasket 40 are preferably formed with an identical shape and structure. Having the same structure reduces the overall cost of manufacture of the hemostasis valve 10. A detailed description of the proximal valve gasket 20 as shown in FIGS. 3-6C is set forth below. For purposes of this discussion, the description of the structure and shape of the proximal valve gasket 20 applies equally to the structure of the distal valve gasket 40 as shown in FIGS. 3-5 and 7A-7C. The hemostasis valve 10 is assembled by aligning and inserting one or more, preferably two, positioning protrusions 32 on the proximal valve gasket 20 and one or more, preferably two, positioning protrusions 52 on the distal valve gasket 40 within one or more, preferably two, positioning slots 34, 54 located on each of the valve gaskets 20, 40 as shown in FIG. 5. The hemostasis valve 10 is inserted into the valve housing 90 at its proximal end 92, as shown in FIG. 3. The cap 80 is then secured onto the proximal end 92 of the valve housing 90.

Upon assembly, a guiding cone or conical receiving area 22 of the proximal valve gasket 20 is approximately in alignment with an opening 84 through the cap 80, as shown in FIG. 4. An inner circular section 82 of the cap 80 that extends outward from the inner surface of the cap 80 may impose a slight axial compression of the proximal valve gasket 20 against the distal valve gasket 40 after assembly of the hemostasis device 70.

The entry face 21 of the proximal valve gasket 20 and the exit face 41 of the distal valve gasket 40 each contain elevated concentric rings 30, 50 as shown, for example, in FIGS. 4, 5, 6A, 6C, 7A, and 7C, which are compressed when the hemostasis valve 10 is inserted within the valve housing 90 and secured in place when the cap 80 is secured to the proximal end of the valve housing 90. The pressure against the hemostasis valve 10 may compress it from about 2 to 5 percent within the valve housing 90.

Figure 6A:
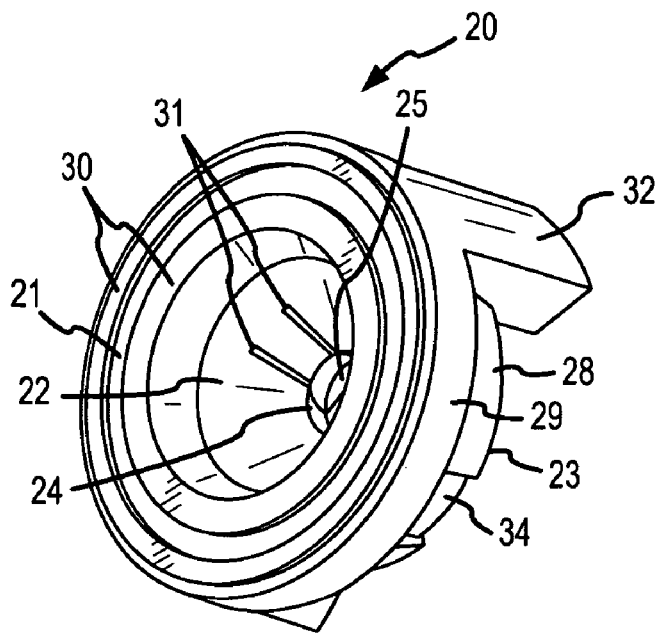
FIG. 6A is a front isometric view of the proximal valve gasket of FIG. 5.
Figure 6B:
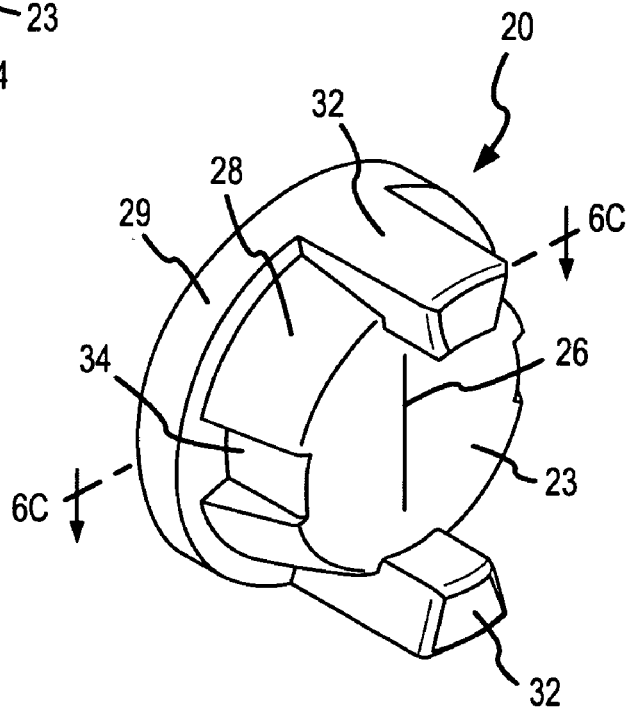
FIG. 6B is a rear isometric view of the proximal valve gasket of FIG. 5.
Figure 6C:
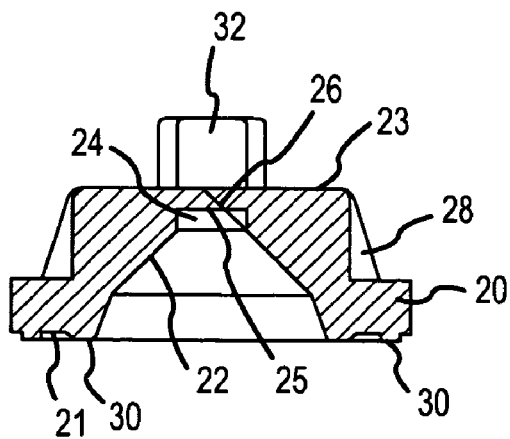
FIG. 6C is a top plan view in cross-section of the proximal valve gasket as indicated in FIG. 6B.

The proximal valve gasket 20 contains a conical receiving area 22 or guiding cone which tapers into a centering or guiding hole 24, as shown in FIGS. 4, 5, 6A and 6C. The conical receiving area 22 tapers at an angle from about 20 to about 80 degrees, and preferably from about 20 to about 60 degrees from the entry face 21 of the valve gasket 20. Alternatively, the receiving area 22 may be formed as a concave surface, for example, following the radius of a spherical shape, rather than as a tapered surface. The centering hole 24 acts as a sealing neck when a catheter of larger diameter passes through the hemostasis valve 10. The centering hole 24 can be formed in any cross section, consistent with the outer geometry of any leads inserted therein. For example, the cross section of this centering hole 24 could be rectangular, triangular, elliptical, or circular. If a circular cross section cross section is utilized for the centering hole 24 as shown in FIGS. 5, 6A, and 6C, the diameter is preferably the same as that of the smallest lead that is utilized with the hemostasis device 70. A circular cross section is preferred as would accommodate a 4 French (1.33 mm) dilator. The centering hole 24 terminates distally in a flat surface 25. Taken together the guiding or centering hole 24 and the conical receiving area 22 guide a lead to the center of the proximal valve gasket 20 of the hemostasis valve 10 to permit easy insertion of a wide variety of leads with different diameters into and through the hemostasis valve 10 while still providing excellent "feel" for clinicians.

Extending distally from the guiding hole 24 of the proximal valve gasket 20 is the slit 26 of the proximal valve gasket 20, which entirely passes through the remaining portion of the proximal valve gasket 20, to its exit face 23 as shown in FIGS. 4 and 6A-6C. This slit 26 is preferably a single slit with its proximal end located at or near the center of the guiding hole 24. The width of the slit 26 may be between about 0.070 in. (1.8 mm) and 0.25 in. (6.4 mm).

Figure 7A:
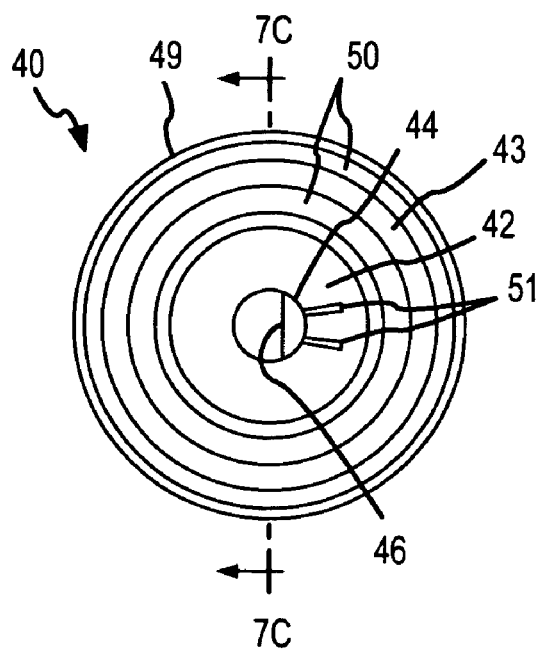
FIG. 7A is a bottom plan view of the distal valve gasket of FIG. 5.

As shown in FIGS. 4, 6A, and 6C, the slit 26 is preferably cut at an angle from about 5 to about 70 degrees from normal to the outer surface 23 of the proximal valve gasket 20. Optimally the angle of this cut is from 44-46 degrees from normal. The slit 26 is preferably axially centered so that its proximal edge and distal edge are equidistant from the central axis of the hemostasis device 70. The slit 26 is also centered radially about the center of the hemostasis device 70. Because the width of slit 26 is preferably greater than the inner diameter of centering hole 24, the slit 26 extends partially over and partially under conical area 22, leaving two sections 31 of slit 26 visible as shown on FIG. 4. (See the corresponding cut sections 51 of the slit 46 in the distal valve gasket 40 as shown in FIG. 7A.) Angling the slit 26 in the manner described creates thin regions of elastomeric material at the leading and trailing portions of the slit 26 and thus makes those areas more responsive to the surface geometry of the lead, which may be placed therein. Because the thin areas of the elastomer conform to the surface geometry of the lead, the ingress of air and other vascular contaminants is also better prevented. Likewise, egress of blood between the lead and inner regions of the hemostasis valve 10 is reduced.

The exit face 23 of the proximal valve gasket 20, includes a depressed, beveled edge 28, as shown in FIGS. 6A-6C, at an angle from about 20 to about 90 degrees, preferably from about 30 to about 60 degrees, from the exit face 23 of the proximal valve gasket 20. By beveling edges 28 of the proximal valve gasket 20, when a lead is extended through the hemostasis valve 10, the blood pressure acting on the hemostasis valve 10 is generally converted from an axial pressure to a radial pressure producing a seamless pair of valve gaskets 20, 40, thereby producing a better "feel" for the clinician. In addition, the material of the beveled edge 28 of the proximal valve gasket 20 expands radially when the indwelling lead is inserted through the hemostasis valve 10. The space between the beveled edge 28 of the proximal valve gasket 20 and the inner surface of the valve housing 90 is gradually filled with the expanded material of the proximal valve gasket 20, thereby reducing the difficulty of introducing the lead through the hemostasis valve 10.

The distal valve gasket 40, as shown in FIGS. 3-5 and 7A-7C, forms the second half of the hemostasis valve 10. The distal valve gasket 40 is designed to complement the proximal valve gasket 20 and operate in coordination therewith to provide improved sealing for small leads. The distal valve gasket 40 is designed with the same shape as that of the proximal valve gasket 20, only reversed, such that the entry face 41 of the distal valve gasket 40 cooperates with the exit face 23 of the proximal valve gasket 20, as shown in FIGS. 4 and 5. The distal valve gasket 40 also includes a beveled edge 48. This beveled edge 48 of the distal valve gasket 40 works in coordination with the beveled edge 28 of the proximal valve gasket 20. The beveled edge 48 is angled at the same angle as the angle of the beveled edge 28 of the proximal valve gasket 20. Using valve gaskets 20, 40 of the same shape provides several advantages. For example, one mold can produce parts that can serve as either gasket. Similarly, the same processes can be used to stock and handle inventory parts.

Figure 7B:
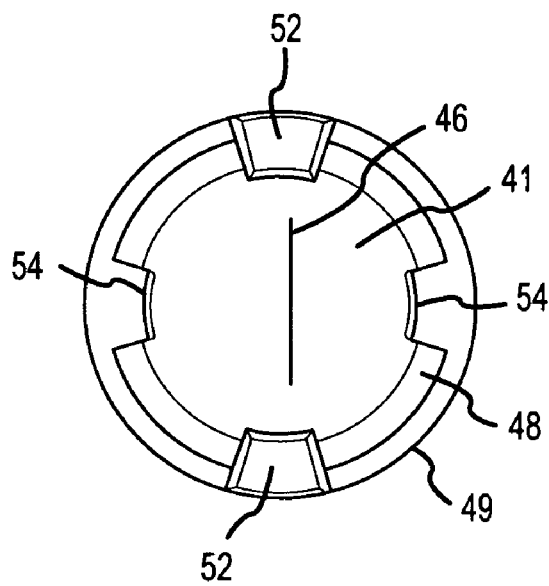
FIG. 7B is a top plan view of the distal valve gasket of FIG. 5.
Figure 7C:
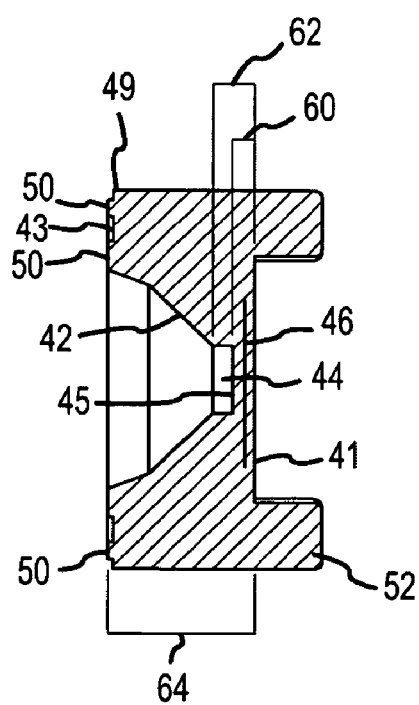
FIG. 7C is an elevation view in cross-section of the distal valve gasket as indicated in FIG. 7A.

Near the center of the distal valve gasket 40 is its slit 46, as shown in FIGS. 7A-7C, which is preferably placed in a position perpendicular to the position of the slit 26 of the proximal valve gasket 20 when the proximal valve gasket 20 and the distal valve gasket 40 are joined together as shown in FIGS. 4 and 5. The width of the slit 46 of the distal valve gasket 40 is preferably the same width as is the width of the slit 26 of the proximal valve gasket 20. The slit 46 of the distal valve gasket 40 extends through the distal valve gasket 40 to a guiding or centering hole 44 as shown in FIG. 7A. The centering hole 44 of the distal valve gasket 40 performs an important function by assisting in the guiding of indwelling leads through the hemostasis valve 10, especially curved leads. When such curved leads pass through the centering hole 24 and the slit 26 of the proximal valve gasket 20, the curved leads may tend to stray from the center of the hemostasis valve 10. By having a second centering or guiding hole 44 present in the distal valve gasket 40, the curved leads passing through the hemostasis valve 10 are encouraged to pass straight through the hemostasis valve 10. The centering hole 44 originates proximally at flat surface 45.

In order to reduce the resistance of the hemostasis valve 10 to the passage of leads therethrough, it is desirable to maintain a minimal distance through the hemostasis valve 10. This may be accomplished using the hemostasis valve 10 of the present invention with the "back-to-back" arrangement of the proximal valve gasket 20 against the distal valve gasket 40. By this "back-to-back" arrangement, the thickness of the hemostasis valve 10 where the medical device passes through the hemostasis valve 10 is minimized. For example, the thickness of the slit area 60 (between exit face 23 and flat surface 25, and between entry face 41 and flat surface 45, respectively) of both the proximal and distal valve gaskets 20, 40 may be between 0.010 inches (0.25 mm) and about 0.03 inches (0.8 mm). This thickness measurement is designated by reference number 60 in FIG. 7C with respect to slit 46. The longitudinal thickness of the centering hole 44 is approximately the same thickness as is the thickness of the slit area 60. Thus, the overall longitudinal thickness of the slit area 60 and centering hole 44 in combination (designated by numeral 62) may be between about 0.02 inches (0.5 mm) and about 0.06 inches (1.6 mm).

In contrast, the thickness of the proximal valve gasket 20 or the distal valve gasket 40 from their respective entry faces 21, 41 to their respective exit faces 23, 43 (designated by number 64) is considerably thicker than the thickness of the respective slit area 60 for slits 26, 46, or the thickness of the respective slit area 60 and centering holes 24, 44 combined (designated by reference number 62). In determining the thickness of the distal valve gasket 40 (or likewise the proximal valve gasket 20), the thickness is measured from its entry face 41 on the proximal side of the distal valve gasket 40 to its exit face 43 on the distal side of the distal valve gasket 40. This thickness of the distal valve gasket 40 (designated by number 64) may be between about 0.07 inches (1.8 mm) and about 0.15 inches (3.8 mm). Thus, preferably, the thickness 60 of the slit 46 of the distal valve gasket 40 is less than about 25 percent of the overall thickness 64 of the distal valve gasket 40 and more preferably from about 10 to about 40 percent of that thickness 64.

The slit 26 of the proximal valve gasket 20 and the slit 46 of the distal valve gasket 40 together act as the primary crisscross sealing barrier to prevent the flow of blood and air through the hemostasis valve 10. In order to assure the proper alignment of the proximal valve gasket 20 and its slit 26 with the slit 46 of the distal valve gasket 40, one or more, preferably two, positioning protrusions 32 are provided in the outer edge 29 of the proximal valve gasket 20 which align with one or more, preferably two, positioning slots 54 present in the outer edge 49 of the distal valve gasket 40, as shown in FIG. 5. By aligning the respective positioning protrusion(s) 32 of the proximal valve gasket 20 with the positioning slot(s) 54 of the distal valve gasket 40, the respective slits 26, 46 align radially, perpendicularly to each other to assure proper relative position of the distal valve gasket 40 and the proximal valve gasket 20 and to form the preferred crisscross sealing pattern within the hemostasis valve 10, as shown in FIGS. 4 and 5. In addition, in one embodiment the slit 46 of the distal valve gasket 40 is located at a position between the respective positioning protrusions 52, as shown on FIG. 7B, and is perpendicular to a line formed between the respective positioning slots 54. The proximal valve gasket 20 contains a similar structure for its slit 26 as shown in FIGS. 6B and 6C. Although the gaskets 20, 40 may be aligned so that the respective slits 26, 46 align perpendicular to each other, the slits 26, 46 may also be aligned so that the angle between the slits 26, 46 is as much as 45 degrees from perpendicular, or more, if desired.

This structure of complimentary positioning protrusions 32, 52 and positioning slots 34, 54 in each of the proximal and distal valve gaskets 20, 40 results in the proper alignment of the proximal valve gasket 20 in relation to the distal valve gasket 40 when the two gaskets are joined together. In addition, the distance between the inner surface of each pair of positioning protrusions 52, as shown in FIG. 7B, may be slightly less than the inner diameter of the slots 54 provided in the distal valve gasket 40. With this structure, when the respective positioning protrusions 32 of the proximal valve gasket 20 are forced within the slots 54 of the distal valve gasket 40, there is an outward pressure placed on the respective positioning protrusions 32. This outward pressure slightly stretches the slit 26 of the proximal valve gasket 20 as it is pulled toward the respective protrusions 32. This provides a better seal to prevent the flow of blood through the hemostasis valve 10 and forces the slit 26 tightly closed even when no indwelling lead is present within the hemostasis valve 10.

When using the angled slit 26 as shown in FIGS. 6A and 6C, the trailing or distal edge of the slit 26 exits the proximal valve gasket 20 at exit face 23. Because the distal slit 46 is perpendicular to proximal slit 26, they intersect at a single point. When the proximal valve gasket 20 and distal valve gasket 40 are in operative engagement, the distal edge of the proximal slit 26 is urged closed by entry face 41. Thus, the thinner distal elastomeric region of the slit 26 retains its ability to conform to the outer diameter of an indwelling lead, but shares the added benefit of being urged closed by the less elastomeric, thicker entry face 41. Similarly, the leading or proximal edge of the distal slit 46 enters the distal valve gasket 40 at the exit face 23. Thus, the exit face 23 supports the thinner proximal elastomeric region of the slit 46, which, again, retains its ability to conform to the outer diameter of an indwelling lead. The axial distal edge of slit 46 also has a thin region. This region is thin and pliant to follow the contour of the lead, but it is urged closed by pressure exerted from a fluid (blood) column in communication with the normally pressurized circulatory system.

The three thin elastomeric regions of the slits 26 and 46 are not only more responsive to the lead contours, they more quickly relax from a state of deflection, sometimes constantly for a period of many hours, to completely isolate the blood from the operating room environment. In other words, the thin regions allow the hemostasis valve 10 to close completely and quickly because they relax to the closed state faster than thicker regions that have been deformed for lengthy periods of time.

The entry face 21 of the proximal valve gasket 20 may have the same structure and shape as the exit face 43 of the distal valve gasket 40. Each of these faces 21, 43 may include one or more concentric rings 30, 50 raised above the surface of the faces 21, 43. For example, in FIGS. 5, 6A, 6C, 7A, and 7C, the two concentric rings 30, 50 are provide on the faces 23, 43 of the valve gaskets 20, 40, irrespectively. The concentric rings 50 are raised slightly above the surface of the exit face 43. The concentric rings 30 are raised slightly above the surface of the entry face 21. Each of these concentric rings 30, 50 is put under pressure when the cap 80 is secured onto the valve housing 90 as shown in FIG. 4. A lesser amount of elastomeric material is placed under pressure because the concentric rings 30, 50 are raised. As a result a better circumferential seal is formed within the valve housing 90 by the hemostasis valve 10 against blood flow around the outside of the hemostasis valve 10 when no lead is present within the hemostasis valve 10.

Figure 11A:
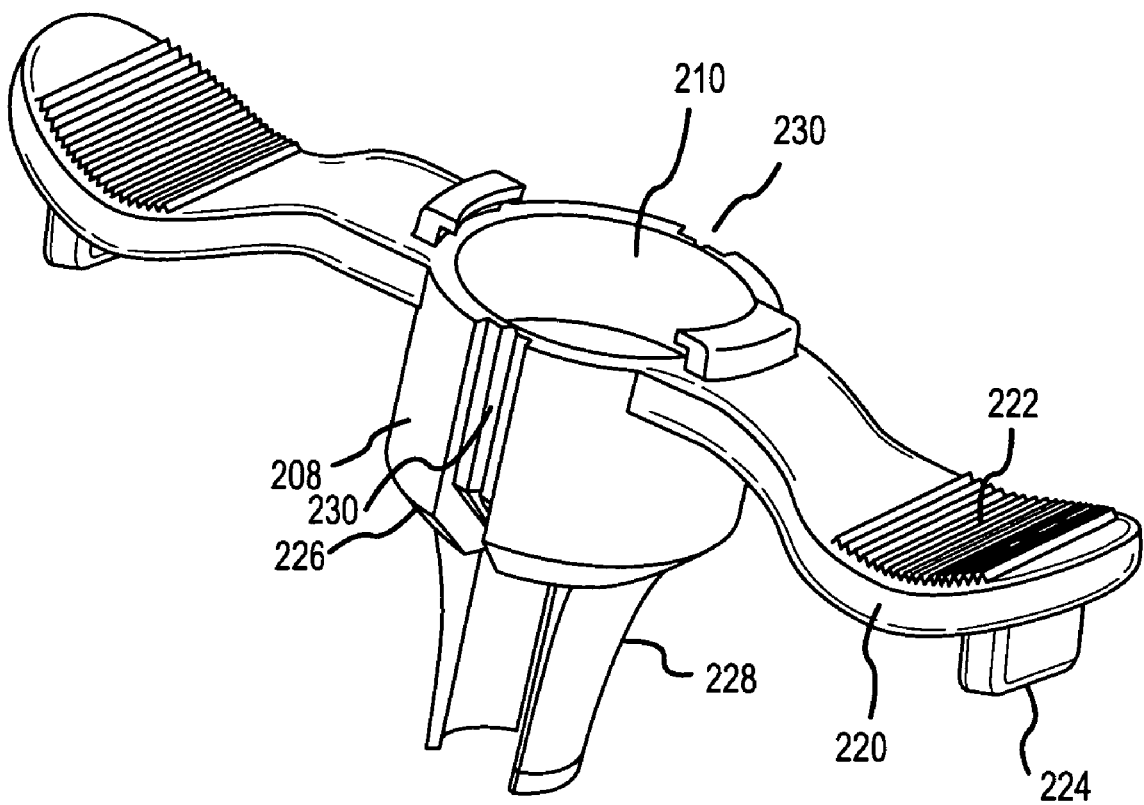
FIG. 11A is a top isometric view of the sheath hub of the assembly of FIG. 1.
Figure 11B:
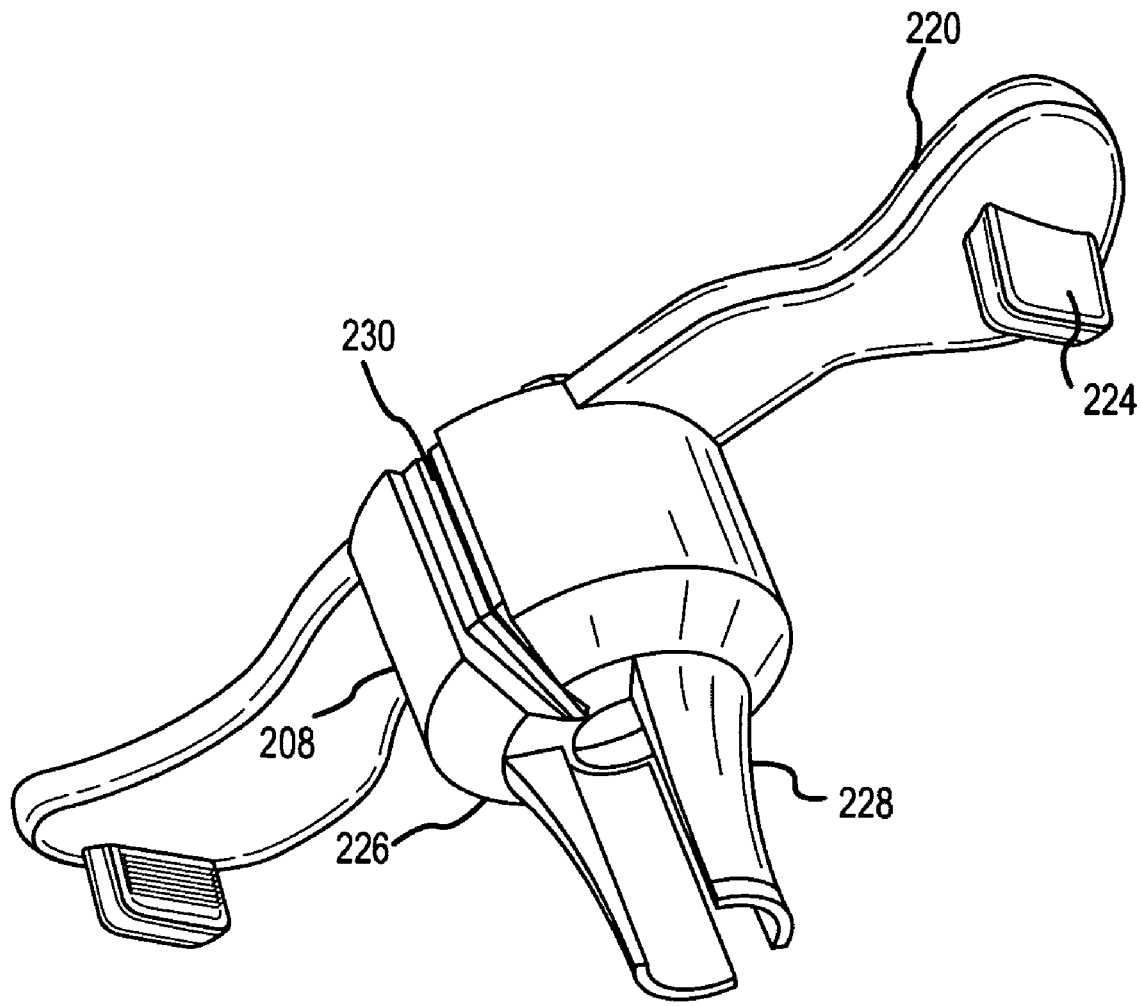
FIG. 11B is a bottom isometric view of the sheath hub of the assembly of FIG. 1.

The splittable sheath 100 is provided as part of the assembly and is adapted at its proximal end to interface with the cannula portion 200. A sheath hub 208 may be attached to the proximal end of the sheath 100. The sheath hub 208 defines an annular wall with an inner surface 210, as shown to good advantage in FIGS. 11A and 11B. The distal portion of the sheath hub 208 tapers as a frustum 226 to a circumference at which it interfaces with the proximal end of the splittable sheath 100, matching the diameter of the sheath 100. A hub snap ring 212 is formed as an annular bump along the inner surface 210 of the sheath hub 208, proximal to the point at which the sheath hub 208 begins to taper, thereby narrowing the inner diameter of the sheath hub 208 at the hub snap ring 212. A pair of hub tabs 228 extend distally from the frustum 226 of the sheath hub 208 along the outer walls of the sheath 100 and are positioned 180 degrees apart. A pair of handles 220 may extend laterally from and normal to the outer wall of the sheath hub 208 in line with the each of the hub tabs 228.

The splittable sheath 100 may be a generally elongated, substantially cylindrical tube formed by extrusion of any suitable biocompatible, thermoplastic material, for example, high density polyethylene (HDPE), polypropylene, fluoropolymer, tetrafloroethylene, polyether block amide (PEBA), polyamide (PA), polyvinyl chloride (PVC), polyurethane-based thermoplastic elastomer, or a blend of any of the aforementioned polymeric materials. A multilayered tubular structure may also be used to co-extrude the introducer sheath 100 using different combinations of these polymeric materials. A preferred material is a polyether-block co-polyamide polymer such as Pebax® (AUTOFINA Chemicals, Inc., Philadelphia, Pa.), which may further be coated with siloxane, wherein the plastic is compatible with body fluids, particularly blood. Additionally, the sheath material may include a radiopaque filler material for better response to fluoroscopy or other imaging methods.

The splittable sheath 100 is inserted within the distal end of the sheath hub 208 between the opposing hub tabs 228 and is secured in place to the distal end of the frustum 226 and the hub tabs 228 preferably by heat adhesion or ultrasonic welding. Alternatively, the sheath hub 208 may be overmoulded about the outer wall of the splittable sheath 100. The hub tabs 228 provide sufficient surface area overlap between the sheath hub 208 and the sheath 100 to ensure adequate mechanical bonding between the components.

Figure 8A:
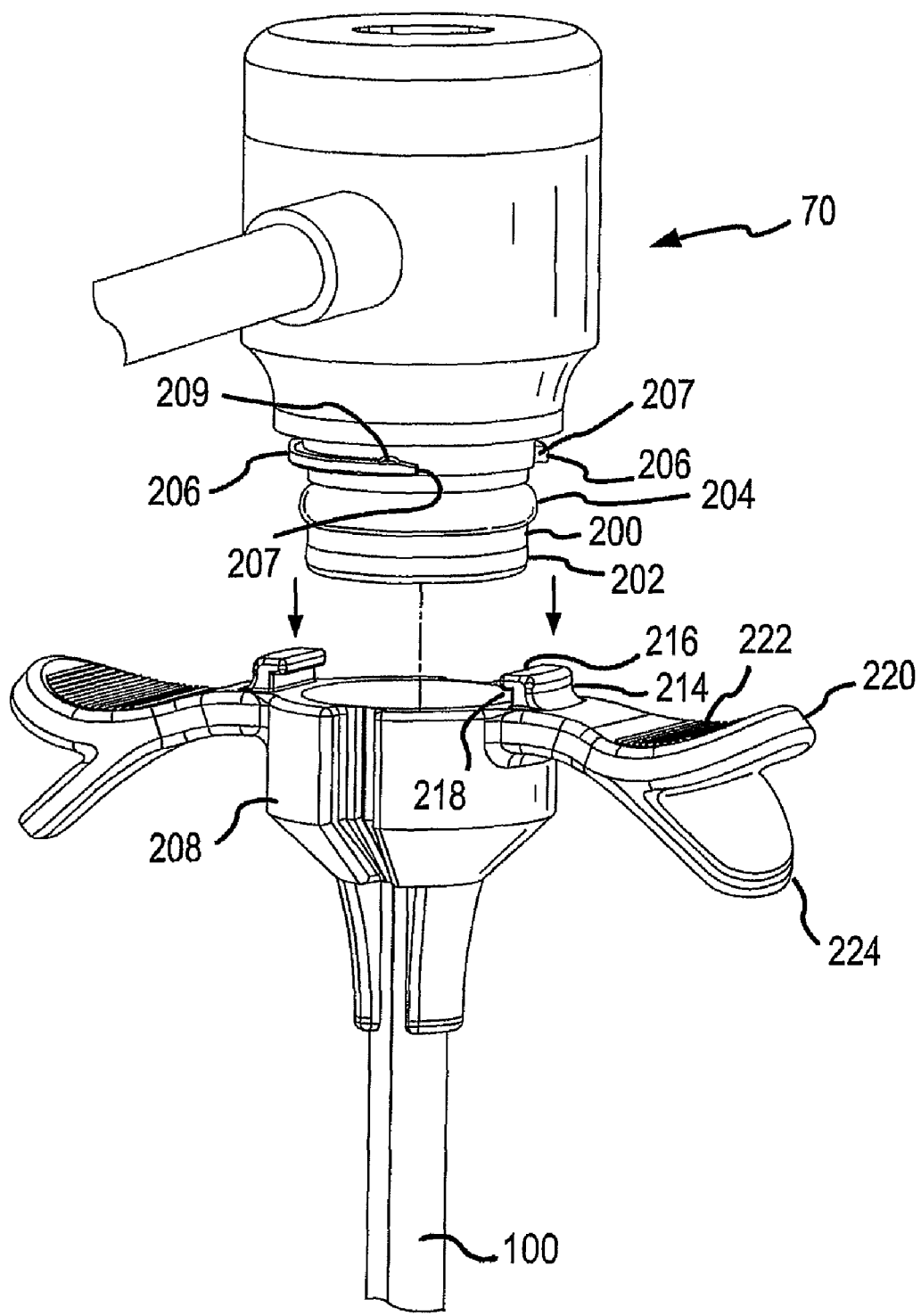
FIG. 8A is an isometric view of a hemostasis device and splittable sheath assembly according to a second embodiment of the invention before coupling.
Figure 8B:
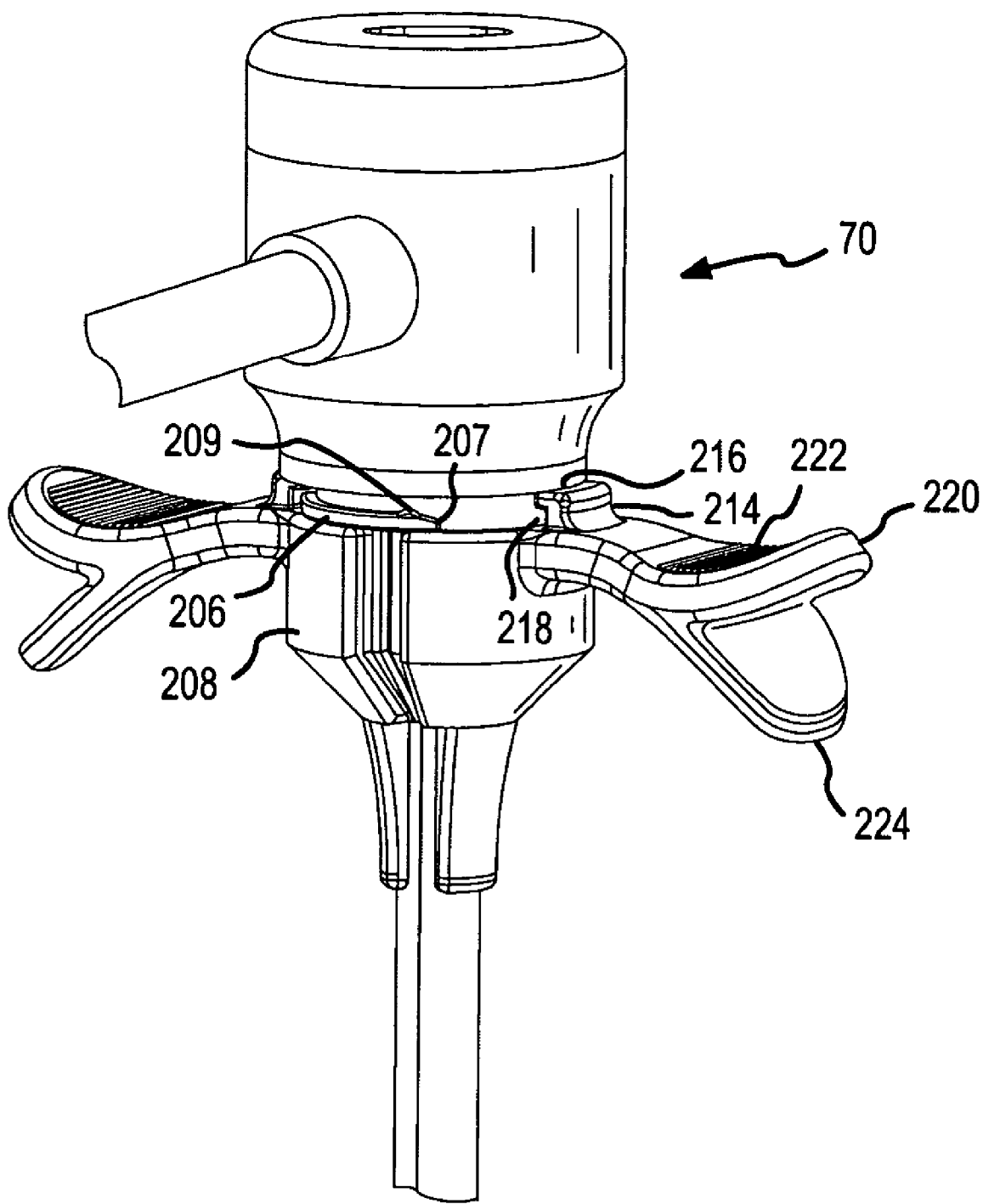
FIG. 8B is an isometric view of the assembly of FIG. 8A with the hemostasis device and splittable sheath assembly partially coupled.
Figure 8C:
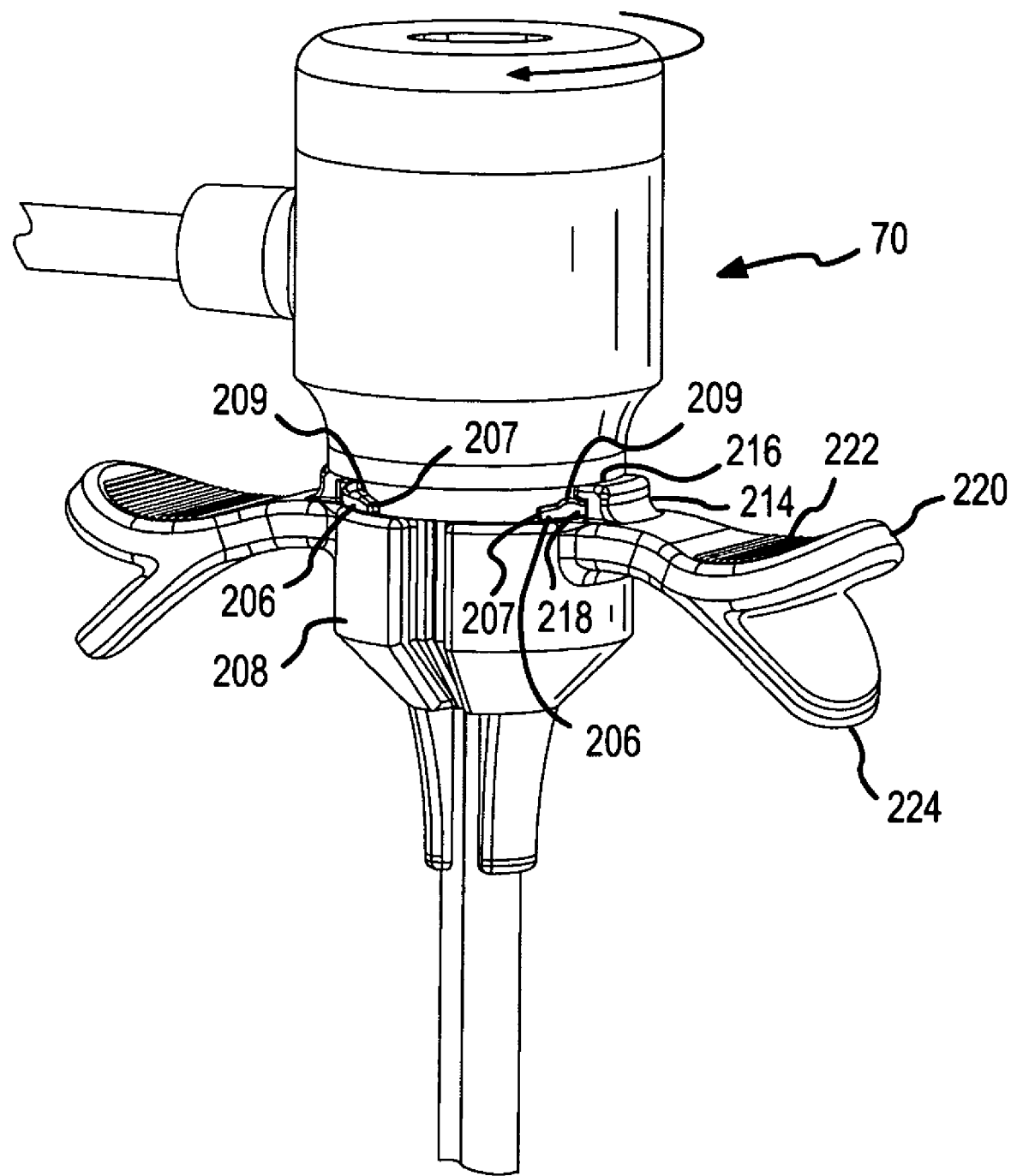
FIG. 8C is an isometric view of the assembly of FIG. 8A with the hemostasis device and splittable sheath assembly fully coupled.
Figure 8D:
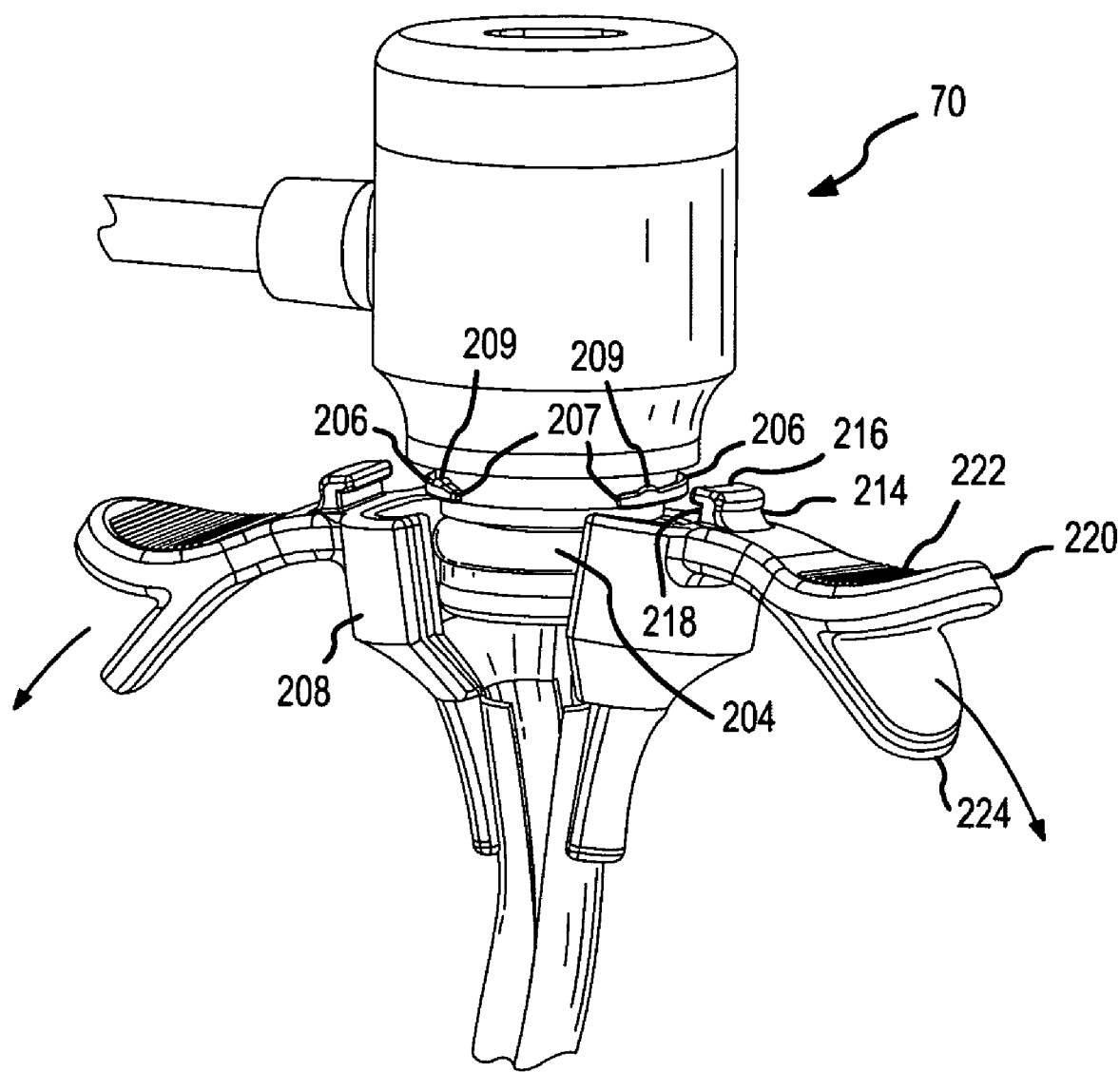
FIG. 8D is an isometric view of the assembly of FIG. 8A with the splittable sheath separated to uncouple from the hemostasis device.
Figure 9A:
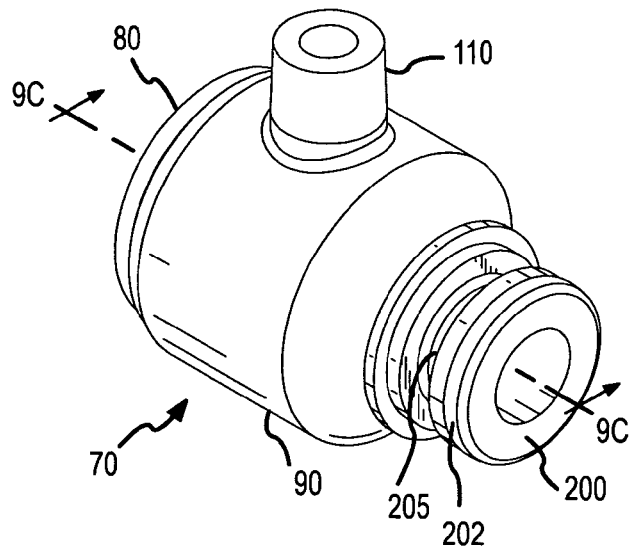
FIG. 9A is an isometric view of an alternative hemostasis device.
Figure 9B:
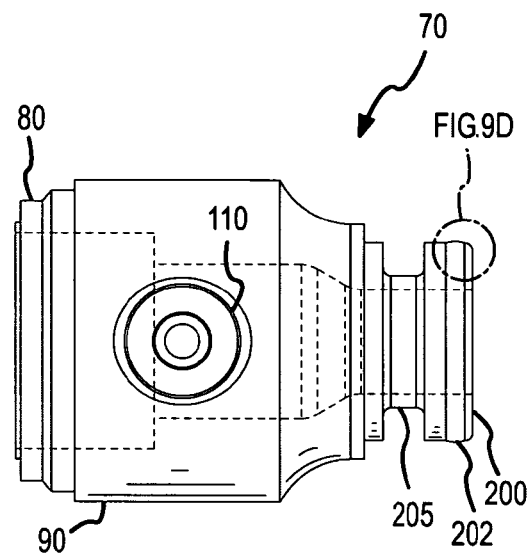
FIG. 9B is a side elevation view of the hemostasis device of FIG. 9A.
Figure 9C:
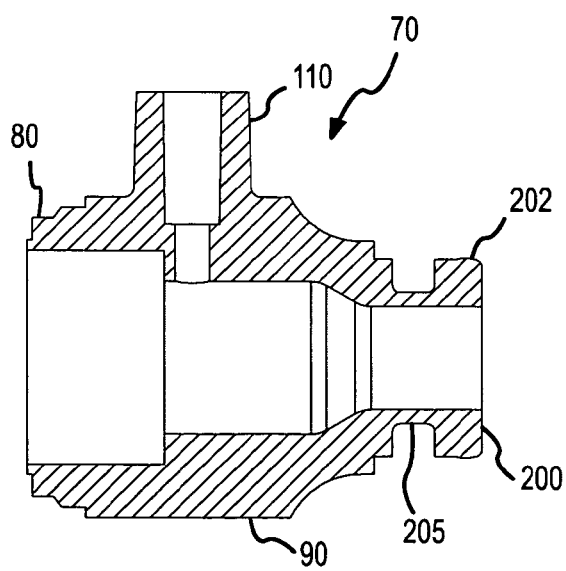
FIG. 9C is a side elevation view in cross-section of the hemostasis device as indicated in FIG. 9A.
Figure 9D:
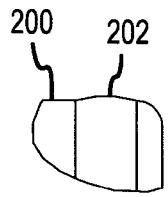
FIG. 9D is a magnified view of an area of the cannula portion of the hemostasis device detailing a snap ring as indicated in FIG. 9B.

As shown in FIGS. 8A-8D, the sheath 100 may also be designed to split in half and tear apart from about an indwelling lead. The sheath 100 has a pair of mechanically formed, longitudinally extending zones of reduced thickness defined by internally scored, longitudinally shallow grooves, or indentations 102 running its length directly opposite each other. The sheath hub 208, as shown to good advantage in FIGS. 11A-11B, likewise has opposing grooves 230 in its outer wall that are oriented in line with the sheath indentations 102. The handles 220 on the sheath hub 208 are positioned 90 degrees apart from each of the grooves 230. When the user places both distal pressure against the top of the handle members 220 and outward radial force by pulling, as indicated in FIG. 8D, both the sheath hub 208 and sheath 100 split along a longitudinal axis for removal from about an indwelling lead.

The sheath 100 maintains the percutaneous opening, or access site to the vasculature, initially made with other devices, such as a hypodermic needle or scalpel, and provides an entrance point for a dilator or obturator, as well as any leads. The introduction of the sheath 100 into the blood vessel is accomplished by a dilator advancing over a guide wire, both of which are advantageously passed through the sheath 100 and hemostasis device 70. Once the sheath 100 is advanced a sufficient distance within the chosen blood vessel, the guidewire and dilator are removed in favor of insertion of other leads. The sheath hub 208 may be molded or otherwise provided with an indicator 232 of the sizes of leads it can accommodate. For example, in FIGS. 1-3, the number "8" is molded into the side of the sheath hub 208 to indicate that lead sizes up to 8 French (1 French=0.33 mm) can be used.

The inner diameter of the sheath hub 208 defined by the inner surface 210 is the same as the outer diameter of the snap ring 202 on the cannula portion 200 of the hemostasis device 70. The remaining surface of the cannula portion 200 is therefore slightly smaller than the inner diameter of the sheath hub. This allows for easy insertion of the cannula portion 200 into the opening in the sheath hub 208 as shown in FIGS. 8A and 8B. Upon insertion of the cannula portion 200 into the sheath hub 208, the cannula snap ring 202 engages the hub snap ring 212. With the exertion of a small amount of pressure, the cannula snap ring 202 slides past the hub snap ring 212 and is engaged on either side by the hub snap ring 212 and the tapering interior surface formed by the frustum portion 226, thereby resisting both distal and proximal movement of the hemostasis device 70. The cannula portion 200 is thereby retained within the sheath hub 208. It should be noted that the annular bumps forming the cannula snap ring 202 and the hub snap ring 212 are very slight and the outward radial force placed on the sheath hub 208 as the snap rings 202, 212 slide past each other is very slight, and is not sufficient enough to cause the sheath hub 208 to begin splitting along the grooves 230.

The outer diameter of the O-ring 204 is similarly larger than the diameter of the outer surface of the cannula portion 200 in order to interface with the inner surface 210 of the sheath hub 208, thereby creating a fluid-tight seal between the hemostasis device 70 and the sheath hub 208. The material chosen for the O-ring 204 should be elastomeric and slightly compressible in order to avoid exerting an outward radial force against the sheath hub 208 of a strength large enough to initiate splitting of the sheath hub 208 along grooves 230.

A second structure may be provided in order to maintain the mechanical engagement between the hemostasis device 70 and the sheath hub 208. As shown in FIGS. 1-4 and 8A-8D, the cannula portion 200 of the hemostasis device 70 may have a pair of external ledges 206 formed opposite each other along the circumference of the outer surface of the cannula portion 200. Each end of each of the ledges 206 may have tapered ends 207 to form a ramp-like surface increasing the width of the ledges 206 from the distal edge to the proximal edge. The ends of the ledges 206 are separated from each other by a pair of gaps where the outer surface of the cannula portion 200 is not covered by the raised ledges 206. A pair of engagement structures in the form of clips 214 are formed adjacent to the proximal end of the sheath hub 208 at the interface between the sheath hub 208 and the opposing handles 220. Therefore, the clips 214 are formed along the same transverse axes as the handles 220 and the hub tabs 228, and are positioned 90 degrees apart from the grooves 230. The clips 214 may extend proximally from the sheath hub 208 and have lips 216 extending radially toward the center of the proximal opening in the sheath hub 208 to define engagement recesses 218 underneath the lips 216. The lips 216 do not extend radially inward beyond the inner surface 210, and therefore do not interfere with the distal end of the cannula portion 200 as it is inserted into and seats within the sheath hub 208.

When engaging the cannula portion 200 with the sheath hub 208, the user should align the ledges 206 with the grooves 230 on the sheath hub 208, or from a different perspective, the user should align the gaps between the ledges 206 with the clips 214. Once the cannula snap ring 202 has moved past the hub snap ring 212 and the cannula portion 200 is seated firmly in the sheath hub 208, the user may then rotate either the hemostasis device 70 or the sheath hub 90 degrees (or both a total of 90 degrees). This will slide the ledges 206 under the lips 216 of the clips 214 into the engagement recesses 218. The tapered ends 207 of the ledges 206 help the ledges 206 start to slide under the lips 216 of the clips 214. The interface between the ledges 206 and clips 214 helps augment the mechanical connection between the hemostasis device 70 and the sheath hub 208 and sheath 100.

One advantage of the present invention is that the hemostasis device 70 may be rotated 360 degrees if needed, for example, to locate the side port 110 in a convenient position for access, without impacting the seal between the cannula portion 200 and the sheath hub 208. In an alternate embodiment depicted in FIGS. 8A-8D, the ledges 206 may further have retention bumps 209. Once the lips 216 of the clips 214 slide fully past the retention bumps 209, the retention bumps 209 help prevent the hemostasis device 70 from inadvertently twisting off of the sheath hub 208.

As shown in FIGS. 1-4 and 11A-11B, the handles 220 extending laterally from the sheath hub 208 may be ergonomically designed for ease of engagement by the fingers of a user. For example, the proximal surface of each of the handles 220 may spread in width and form a concave surface area suited to comfortably receive the thumbs of a user. The proximal surface of the handles 220 may also be grooved to form grips 222 to aid the user's ability to grasp the handles 220. The outer, upturned ends of the handles 220 may likewise aid the user's grasp. The handles 220 may also have nubbins 224 extending from the distal sides in order to aid the user's grasp as well. An alternative nubbin 224 configuration is shown in FIGS. 8A-8D, wherein the nubbins 224 extend as wing-like structures distally from the handles 220. Surfaces of the nubbins 224 may also be grooved to form grips.

In order to remove the hemostasis device 70 from the sheath hub 208, either the hemostasis device 70 or the sheath hub 208 may be rotated 90 degrees to disengage the ledges 206 from the engagement structures 214. Then the hemostasis device 70 may be pulled proximally while the sheath hub 208 is held in place to disengage the cannula portion 200 from the sheath hub 208 and further pulled over the end of any indwelling lead. Alternately, the hemostasis device 70 may remain stationary while the handles 220 are pulled distally and radially outwardly by the user. In this manner, the sheath hub 208 begins to split along the grooves 230. As the sheath hub 208 splits, the engagement structures 214 are pulled radially outward and disengage from the ledges 206, without having to rotate either the hemostasis device 70 or the sheath hub 208, as shown in FIG. 8D. As the user continues to pull, the hub tabs 228 transfer the outward radial and distal forces to the sheath 100 and the sheath 100 will split along the indentations 102 aligned with the grooves 230 in the sheath hub 208. Once the sheath 100 is fully separated, it may be removed from about any indwelling lead. An advantage of this method of disengaging the sheath 100 from the hemostasis device 70 is that rotation of the hemostasis device 70 is prevented. In some instances, for example, in pacemaker lead placement, this method is preferred in order to minimize the risk of dislodging the lead from its placement in the tissue that can occur when moving the hemostasis device 70, which tightly seals around the indwelling lead.

Figure 12:
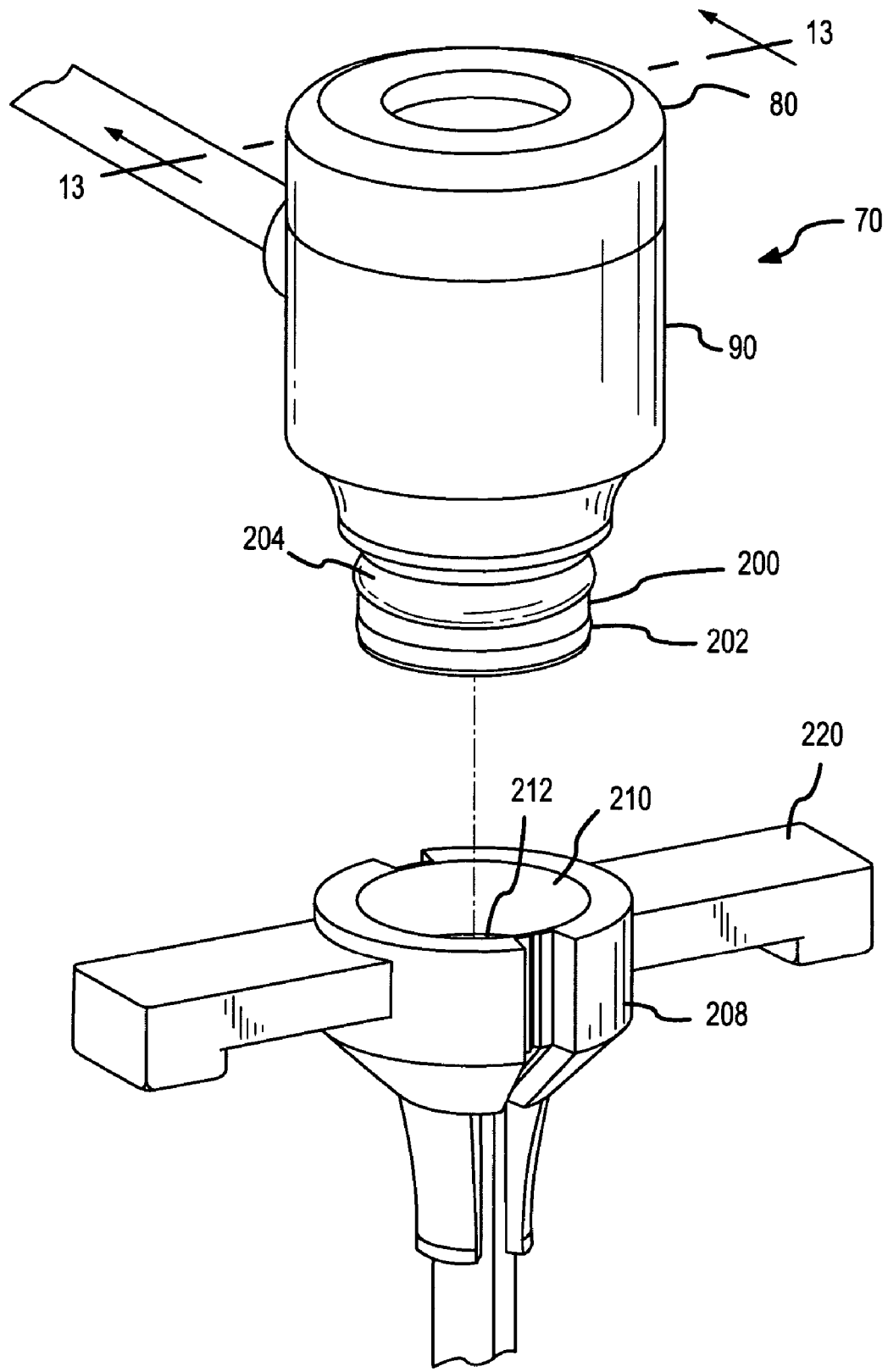
FIG. 12 is an isometric view of a hemostasis device and splittable sheath assembly according to a third embodiment of the invention.
Figure 13:
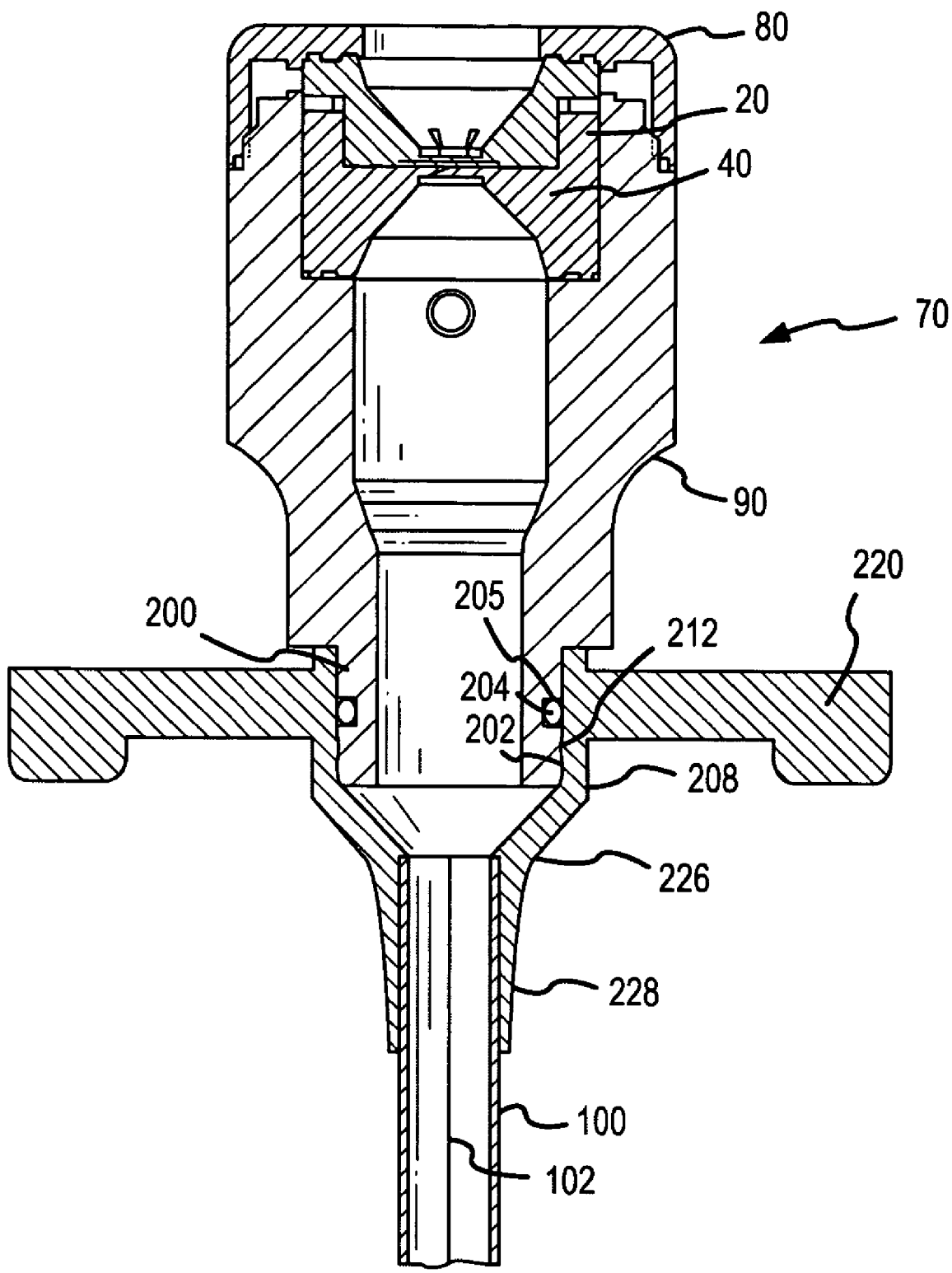
FIG. 13 is an elevation view in cross-section, as indicate generally in FIG. 12, of the assembly of FIG. 12 with hemostasis device coupled with splittable sheath.

FIGS. 9A-10D, 12, and 13 depict alternative embodiments of the present invention. In these embodiments, the cannula portion 200 of the hemostasis device 70, as shown in FIGS. 9A-9D, 12, and 13, is not provided with circumferentially placed ledges. Likewise, the sheath hub 208, as shown in FIGS. 10A-10D, 12, and 13, is not provided with an opposing engagement structure. In these embodiments, a coupling interface between the cannula snap ring 202 and the hub snap ring 212, and additionally the O-ring 204 friction fit within the sheath hub 208, provide the only mechanical engagement between the hemostasis device 70 and the sheath hub 208. The slight sizes of the cannula snap ring 202 and the hub snap ring 212 are shown in detail in FIGS. 9D and 10D, respectively. Designing the snap rings 202, 212 to protrude only minimally is important in order to prevent the inadvertent splitting of the sheath hub 208 and sheath 100. FIGS. 12 and 13 additionally depict the sheath hub 208 with more traditional handles 220 found on prior art splittable sheaths 100.

FIGS. 10B, 10C, and 13 provide additional detail of the interface between the sheath hub 208 and the sheath 100, whereby a fluid-tight seal is formed therebetween. The proximal end of the sheath 100 seats against an annular rim 229 of the sheath hub 208. When the sheath hub 208 is over-molded, ultrasonically welded, or thermally bonded to the sheath 100, the interface between the sheath 100 and the annular rim 229 creates the desired seal. In an alternate embodiment, the sheath hub 208 may be formed integrally with the sheath 100.

Figure 14:
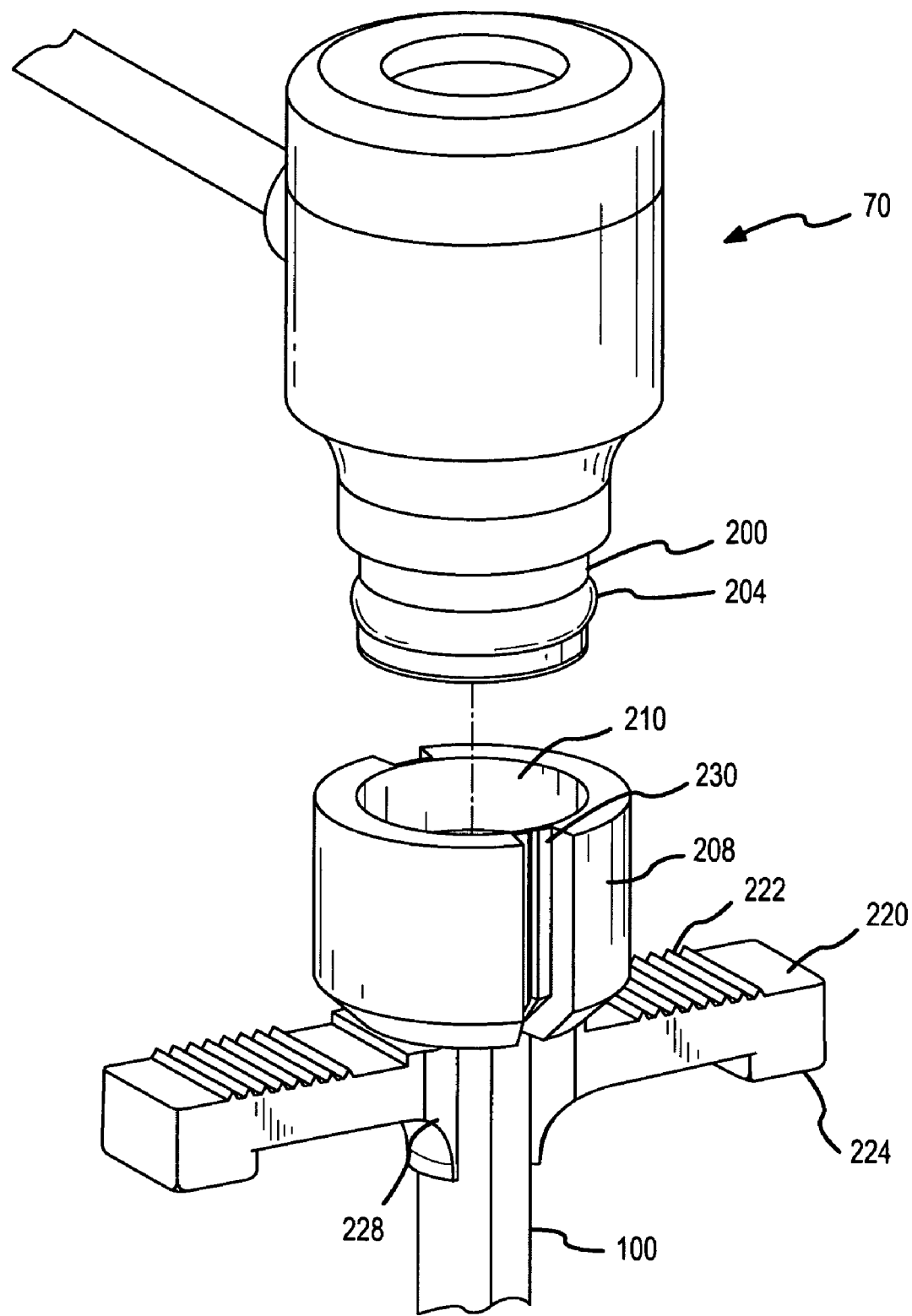
FIG. 14 is an isometric view of a hemostasis device and splittable sheath assembly according to a fourth embodiment of the invention.

FIG. 14 depicts another embodiment of the invention. In this embodiment, the handles 220 are located distally from the sheath hub 208 and are adjacent to the proximal end of the sheath 100 on the hub tabs 228, rather than on the proximal end of the sheath hub 208. In this embodiment, the only mechanical interface between the hemostasis device 70 and the sheath hub 208 is the friction fit between the O-ring 204 and the inner surface 210 of the sheath hub 208. Although functional, this embodiment may be less preferred because of the greater difficulty that may be experienced in initiating the separation of the two halves of the sheath hub 208. Because the handles are placed distally from the sheath hub 208, the transfer of the splitting force to the proximal end of the sheath hub 208 is more difficult than if the handles were located on the proximal end of the sheath hub 208. It should be understood that any combination of engagement and retention structures disclosed herein may be used. For example, the combination of clips 214 and ledges 206 as in the embodiment of FIG. 1 may be used without the snap rings 202, 212, but with the O-ring 204.

Figure 15:
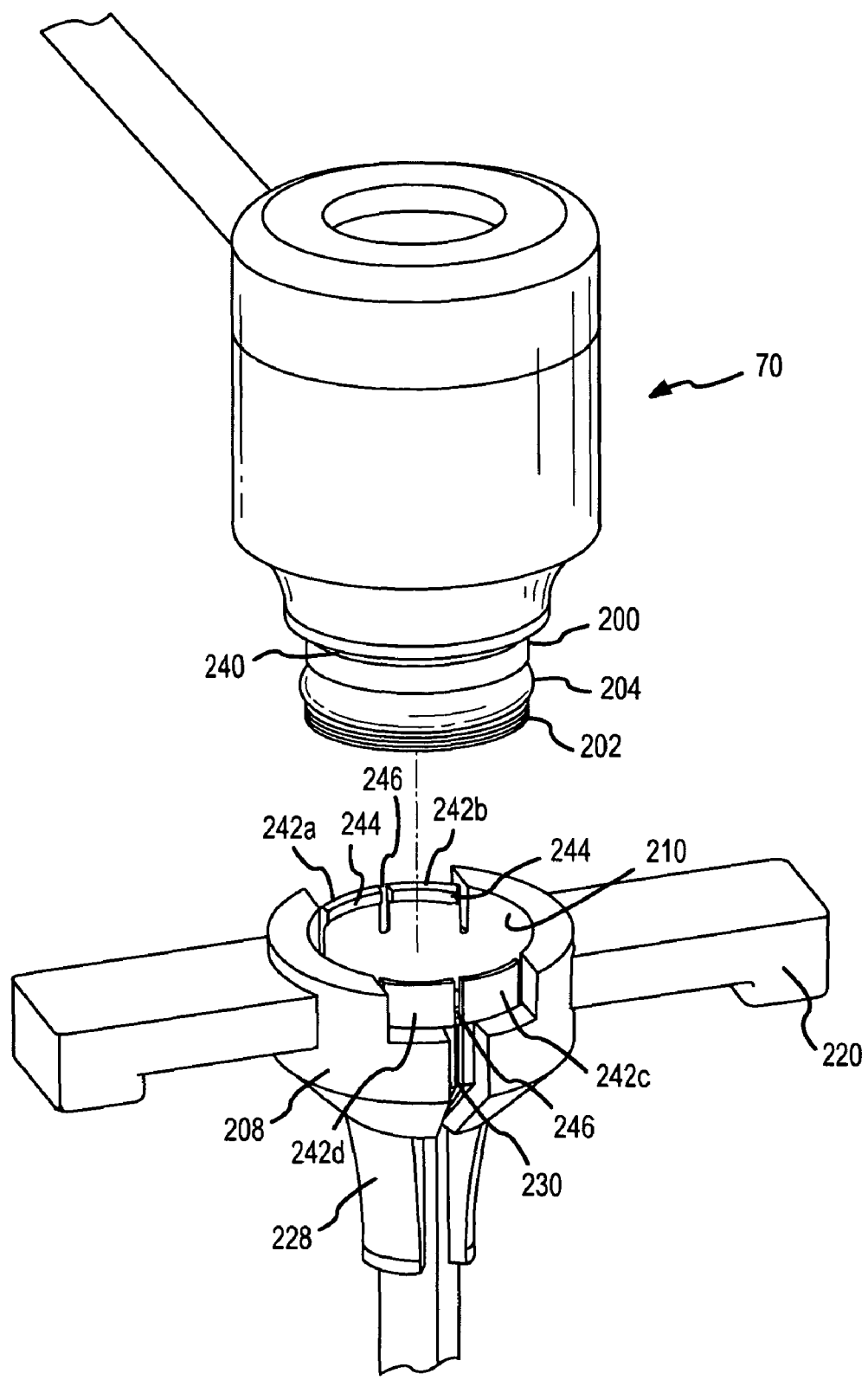
FIG. 15 is an isometric view of a hemostasis device and splittable sheath assembly according to a fifth embodiment of the invention.

FIG. 15 depicts an alternative embodiment of the invention. In this embodiment, in addition to the snap rings 202, 212 (not shown in FIG. 15), and lieu of the ledge structure 206 of FIGS. 1-4, an additional mechanical engagement structure is provided. The sheath hub 208 is formed with a set of four tabs 242a-242d forming part of the annular wall 210. The tabs 242a-242d do not extend beyond the proximal surface of the sheath hub 208. The tabs 242a-242d are formed in pairs 242a, 242b and 242c, 242d, and each pair is aligned longitudinally with grooves 230 in the sheath hub 208. Gaps 246 are further provided between pairs of tabs 242a, 242b and 242c, 242d, wherein the gaps 246 are exactly aligned with grooves 230. Each of the tabs 242a-242d is curved to follow the circumference of the annular wall 210 of the sheath hub 208. Each of the tabs 242a-242d is further formed with a tooth 244 extending radially inward into the lumen of the sheath hub 208. In addition to the cannula snap ring 202 and the O-ring 204, the cannula portion 200 of the hemostasis device 70 is further formed with an annular recess 240 proximal to the O-ring recess 205 (not shown in FIG. 15). In this embodiment, the snap ring 202 is also depicted with a rectangular rather than semi-circular cross-section as an alternative form of the engagement structure.

When the cannula portion 200 is inserted into the lumen of the sheath hub 208, in addition to the interface between the snap rings 202, 212 (not shown in FIG. 15), the teeth 244 of the tabs 242a-242d engage the annular recess 240 to provide additional mechanical connection between the hemostasis device 70 and the sheath hub 208. To disengage the sheath hub 208 from the hemostasis device 70, the user pulls the handles 220 distally and radially outward to initiate the splitting of the sheath hub 208. Because the gaps 246 between the pairs of tabs 242a, 242b and 242c, 242d are aligned with the grooves 230, the teeth 244 of the tabs 242a-242d will easily pull out of the annular recess 240 on the cannula portion 200 and allow the sheath hub 208 to pull apart from about the hemostasis device 70 and any indwelling lead.

Figure 16:
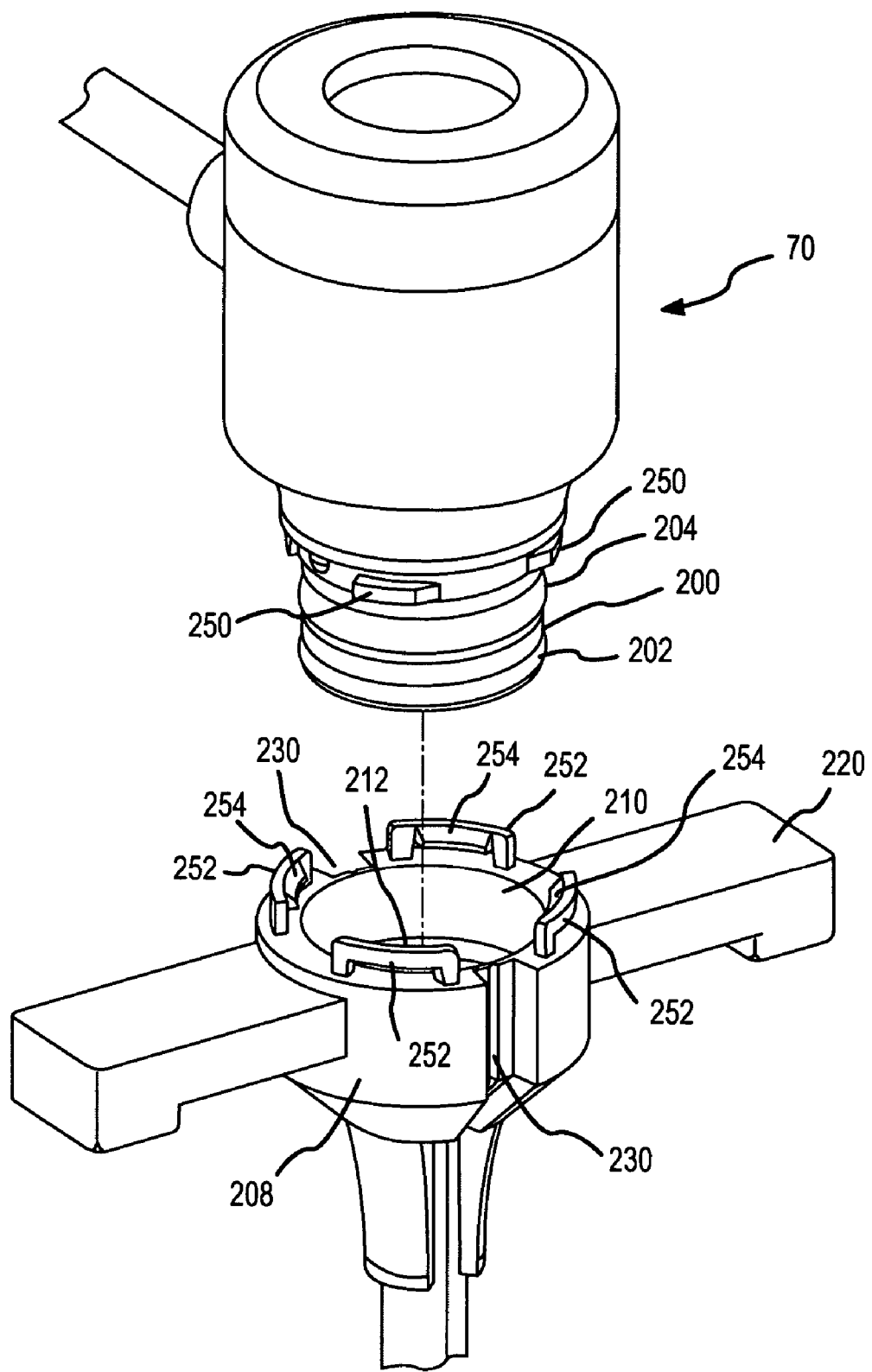
FIG. 16 is an isometric view of a hemostasis device and splittable sheath assembly according to a sixth embodiment of the invention.

FIG. 16 depicts another alternative to the pair of ledges 206 and opposing engagement structures 216 depicted in FIGS. 1-4. In FIG. 16, four independent ledge structures 250 are formed about the cannula portion 200 along the same circumference proximal to the O-ring 204. Opposite these ledge structures 250 on the sheath hub 208, four clips 252 are formed extending proximally from the proximal rim of the sheath hub 208. Each of the clips 252 is curved to follow the circumference of the annular wall 210 of the sheath hub 208. Each of the clips 252 further has a tooth 254 extending radially inward toward the lumen of the sheath hub 208, but does not actually extend beyond the inner wall 210 of the sheath hub 208 so as not to interfere with the cannula portion 200 of the hemostasis device 70 as it is seated in the lumen of the sheath hub 208. Two of the clips 252 are located between the opposing grooves 230 toward one handle 220 and the remaining two clips 252 are positioned between the opposing grooves 230 toward the second handle 220.

In order to engage the hemostasis device 70 with the sheath hub 208, the ledge structures 250 are aligned with the spaces separating the corresponding clips 252. The hemostasis device 70 may then be placed upon the sheath hub 208. When the cannula portion 200 is seated within the lumen of the sheath hub 208 such that the snap rings 202, 212, engage each other, the hemostasis device 70 may then be rotated 45 degrees to engage the ledge structures 250 with the teeth 254 of the clips 252. In order to release the hemostasis device 70 from the sheath hub 208, the hemostasis device 208 may be turned 45 degrees in the opposite direction and pulled proximally by the user to remove the cannula portion 200 from the lumen of the sheath hub 208. When it is undesirable to rotate the hemostasis device 70 or if the procedure calls for removal of the sheath 100, the sheath 100 may merely be split. When a radially outward and distal force is exerted on the handles 220, the sheath hub 208 splits along the areas weakened by the grooves 230 and the clips 252 disengage from the ledge structures 250. The hemostasis device 70 is then disengaged from the sheath hub 208.

Figure 17A:
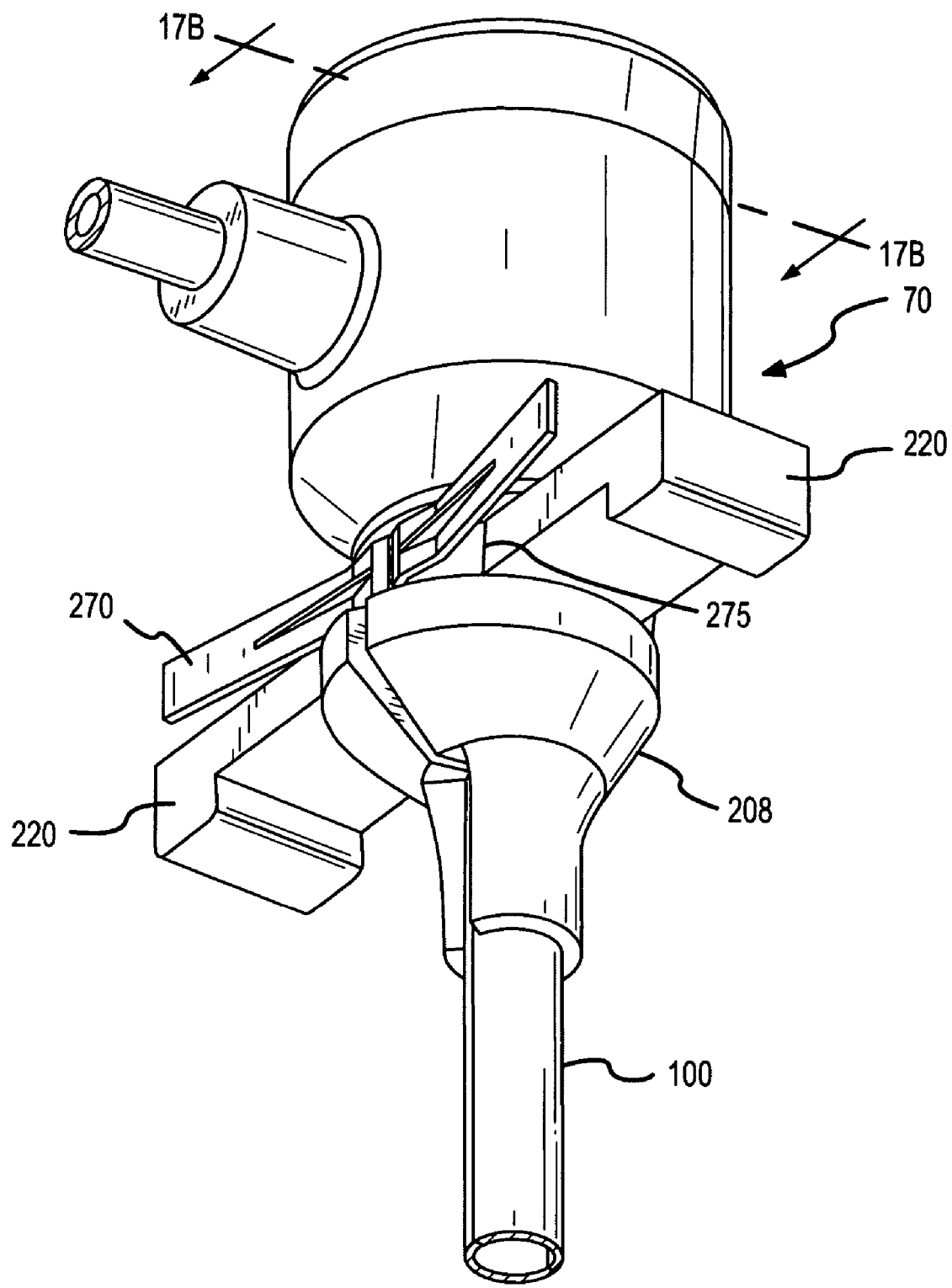
FIG. 17A is an isometric view of a hemostasis device and splittable sheath assembly according to a seventh embodiment of the invention.
Figure 17B:
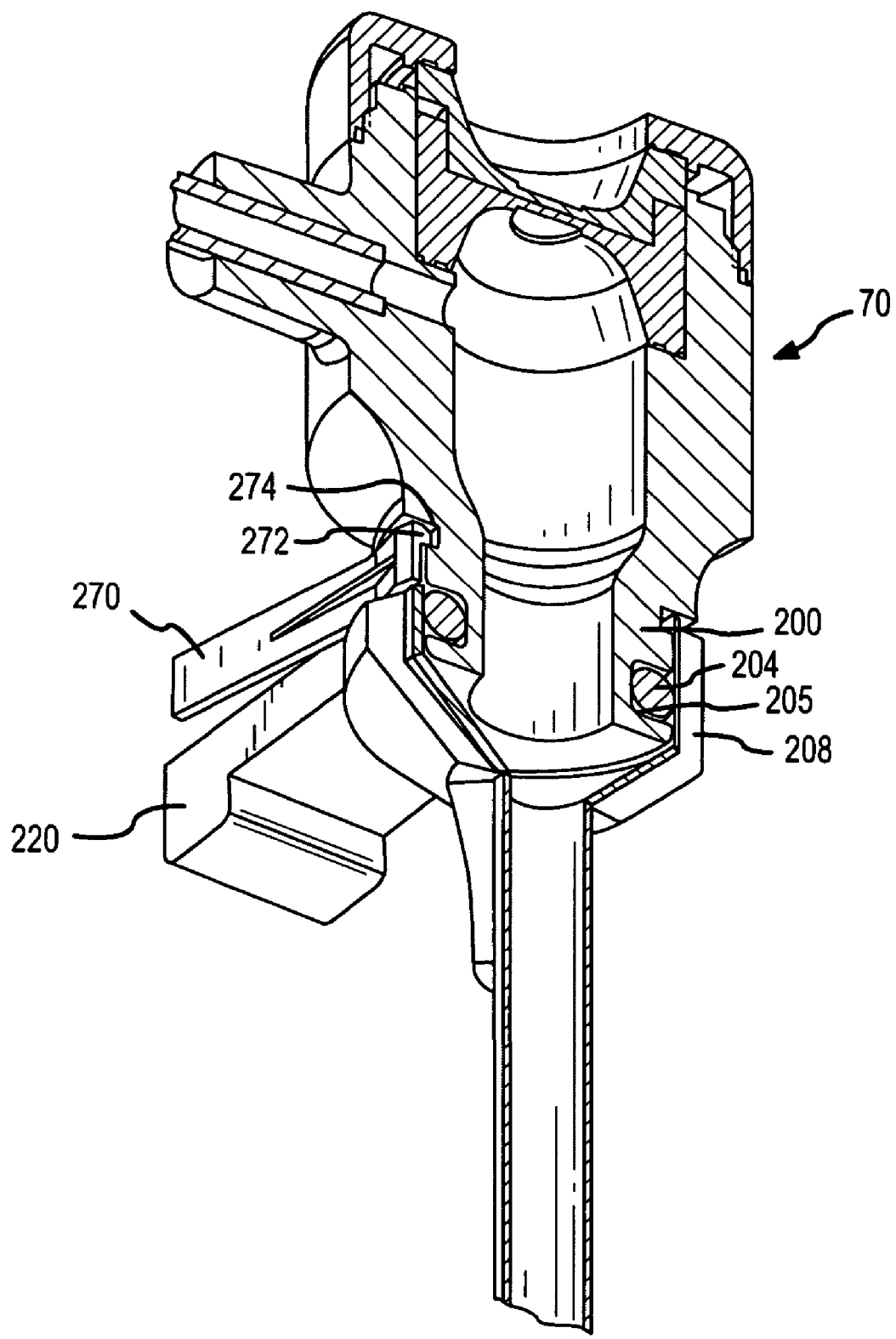
FIG. 17B is an isometric view in cross-section of the assembly as indicated in FIG. 17A.

In yet another embodiment, as shown in FIGS. 17A and 17B, a sheath hub 208 may further be formed with one or more wing tabs 270 positioned over a handle 220. The wing tabs 270 are connected with the sheath hub 208 via a structural hinge 275. The wing tabs 270 may be formed with a tooth 272 to engage a recess 274 in the cannula portion 200 of the hemostasis device 70. In this embodiment, the engagement between the wing tabs 270 and the cannula portion 200 provides the only mechanical connection aside from the friction fit between the O-ring 204 and the annular wall 210 of the sheath hub 208. Although not shown, snap rings 202, 212 as in the previous embodiments could additionally be used. In order to disengage the hemostasis device 70 from the sheath hub 208, the user has two options. The user may press against the wing tabs 270 to remove the teeth 272 from the recess 274 and pull the hemostasis device 70 proximally from the sheath hub 208. Alternately, the user may simply pull on the handles 220 to initiate the splitting of the sheath hub 208 and the sheath 100. The mechanical connection provided by the wing tabs 270 is disengaged when the sheath hub 208 is split, allowing the easy separation of the hemostasis device 70 from the sheath hub 208.

Figure 18A:
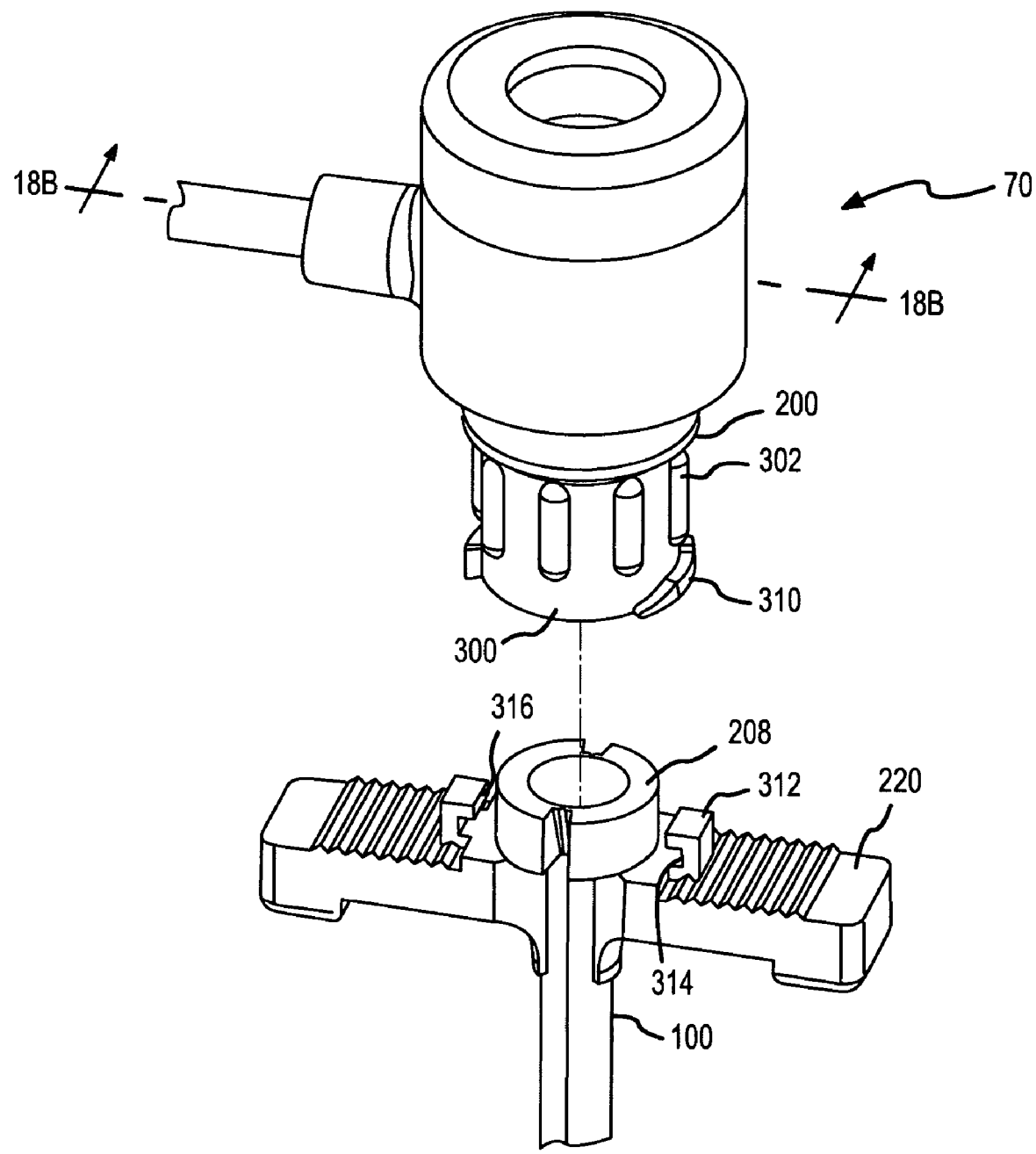
FIG. 18A is an isometric view of a hemostasis device and splittable sheath assembly according to a eighth embodiment of the invention.
Figure 18B:
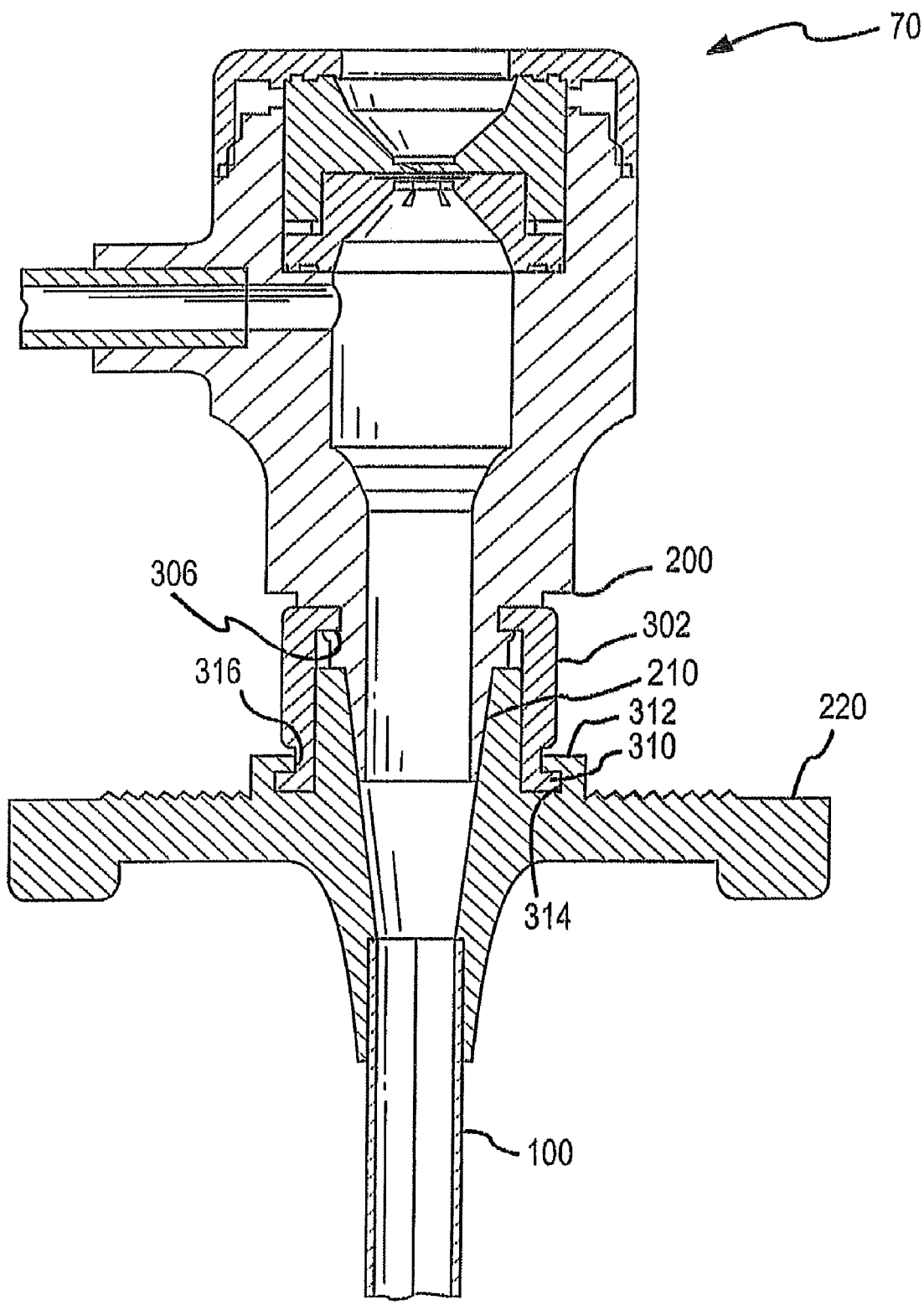
FIG. 18B is an elevation view in cross-section of the assembly as indicated in FIG. 18A.

In an alternative embodiment shown in FIGS. 18A and 18B, a freely-rotating connector nut 300 is retained about the cannula portion 200 by annular ledge 306. This connector nut 300 may be provided with surface knurling 302 to aid in grasping by the user. In this embodiment, the connector nut 300 is externally threaded with a pair of ledges 310. A sheath hub 208 is formed proximal to the handles 220 and is sized to slip within the lumen of the connector nut 300. The cannula portion 200 of the hemostasis device 70 seats within the lumen of the sheath hub 208 to seal with the inner wall 210 of the sheath hub 208. Engagement structures such as clips 312 with radially oriented lips 316 and recesses 314 may extend proximally from each of the handles 220 adjacent to the sheath hub 208. The clips 312 are designed to accept the ledges 310 on the connector nut 300 within the recesses 314 underneath the lips 316. Once the connector nut 300 is placed over the sheath hub 208, it may be rotated 90 degrees to engage and disengage the ledges 310 from the engagement structures 312. Alternately, the sheath hub 208 and splittable sheath 100 may be pulled apart to likewise disengage the splittable sheath 100 and sheath hub 208 from the hemostasis device 70.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A delivery system for delivering a medical instrument, the system comprising
    a hemostasis device having a first engagement structure;
    a splittable sheath;
    a sheath hub joined with a proximal end of the splittable sheath, the sheath hub further having a second engagement structure disposed on a proximal end thereof;
    a third engagement structure disposed on the hemostasis device proximally displaced from the first engagement structure;
    a fourth engagement structure disposed on the sheath hub; and
    a pair of handles joined with the sheath hub, wherein each handle is positioned on an opposing lateral half of the sheath hub; wherein
        the first engagement structure is adapted to engage the second engagement structure to couple the hemostasis device with the splittable sheath;
        the third engagement structure is adapted to engage the fourth engagement structure to axially couple the hemostasis device with the splittable sheath; and the second engagement structure is adapted to disengage from the first engagement structure and the fourth engagement structure is adapted to disengage from the third engagement structure when the opposing lateral halves of the sheath hub are separated from each other in order to split the splittable sheath.

2. The delivery system of claim 1 further comprising a fluid-tight seal for engagement between the hemostasis device and the sheath hub.

3. The delivery system of claim 1, wherein the third engagement structure engages the fourth engagement structure to axially couple the hemostasis device with the splittable sheath without impeding rotational movement between the hemostasis device and the splittable sheath.

4. A delivery system for delivering a medical device, the system comprising
   a hemostasis device having a cannula portion and a first coupler and a first connector disposed on the cannula portion;
   a splittable sheath;
   a bifurcated sheath hub formed of opposing lateral halves joined with a proximal end of the splittable sheath, the bifurcated sheath hub comprising a second coupler and a second connector; wherein
      the first coupler is adapted to engage the second coupler to couple the hemostasis device with the splittable sheath;
      the first connector is adapted to engage the second connector to axially connect the hemostasis valve with the splittable sheath; and
      the second coupler is adapted to disengage from the first coupler and the second connector is adapted to disengage the first connector when the opposing lateral halves of the bifurcated sheath hub are separated from each other to split the splittable sheath.

5. The delivery system of claim 4, further comprising a pair of handles joined with the bifurcated sheath hub, wherein each handle is positioned on one of the opposing lateral halves of the bifurcated sheath hub.

6. The delivery system of claim 4, wherein the bifurcated sheath hub further comprises a pair of tabs, each extending distally from one of the opposing lateral halves of the bifurcated sheath hub and adhered to an outer wall of the splittable sheath.

7. The delivery system of claim 6, further comprising a pair of handles joined with the bifurcated sheath hub, wherein each handle is positioned on one of the tabs, respectively.

8. The delivery system of claim 4, wherein
   the bifurcated sheath hub further comprises an annular wall with an interior surface defining a lumen;
   the hemostasis device further comprises an O-ring disposed about the cannula portion, the O-ring of slightly larger diameter than the interior surface of the annular wall of the bifurcated sheath hub, for creating a fluid-tight seal with the bifurcated sheath hub when the cannula portion is seated within the lumen.

9. The delivery system of claim 4, wherein
   the bifurcated sheath hub further comprises an annular wall with an interior surface defining a lumen;
   the first coupler comprises a first snap ring disposed about a distal end of the cannula portion, wherein the first snap ring is of slightly larger diameter than the interior surface of the annular wall of the sheath hub; and
   the second coupler comprises a second snap ring formed on the interior surface of the annular wall, wherein the second snap ring is of slightly smaller diameter than the diameter of the interior surface of the annular wall adjacent the second snap ring; and
   wherein when the hemostasis device is coupled with the splittable sheath, the first snap ring is positioned distal and adjacent to the second snap ring.

10. The delivery system of claim 4 wherein
    the bifurcated sheath hub further comprises an annular wall with an interior surface defining a lumen;
    the second coupler comprises a pair of clips joined with the bifurcated sheath hub, wherein
       each clip is positioned on and extends proximally from a proximal end of one of the opposing lateral halves of the bifurcated sheath hub, respectively;
       each clip defines a lip and a recess; and
    the first coupler comprises a pair of ledges disposed on opposing sides of the cannula portion;
    wherein when the hemostasis device is coupled with the splittable sheath, each ledge is retained within one of the recesses by one of the lips, respectively.

11. The delivery system of claim 4, wherein
    the bifurcated sheath hub further comprises an annular wall with an interior surface defining a lumen;
    the second coupler comprises two sets of paired tabs, wherein
       each tab forms a portion of the annular wall of the bifurcated sheath hub;
       each tab is positioned on the proximal end of the bifurcated sheath hub;
       the sets of paired tabs are positioned opposite each other;
       each tab in each pair of tabs is positioned apart from the other on one of the opposing lateral halves of the bifurcated sheath hub; and
       each tab further comprises a tooth on its proximal end extending radially into the lumen; and
    the first coupler comprises a circumferential groove about the cannula portion;
    wherein when the hemostasis device is coupled with the splittable sheath, each tooth in each of the tabs is retained within the circumferential groove.

12. The delivery system of claim 4, wherein
    the bifurcated sheath hub further comprises an annular wall with an interior surface defining a lumen;
    the second coupler comprises four clips joined with the bifurcated sheath hub, wherein
       each clip is positioned on and extends proximally from a proximal end of the bifurcated sheath hub;
       each clip is spaced equidistant from each adjacent clip circumferentially about the lumen;
       pairs of the four clips are positioned on one of the opposing lateral halves; and
       each clip defines a lip and a recess; and
    the first coupler comprises four ledges disposed equidistant from each adjacent ledge circumferentially about the cannula portion;
    wherein when the hemostasis device is coupled with the splittable sheath, each ledge is retained within one of the recesses by one of the lips.

13. The delivery system of claim 4, wherein
    the bifurcated sheath hub further comprises an annular wall with an interior surface defining a lumen;
    the second coupler comprises at least one tab positioned on the proximal end of the bifurcated sheath hub, wherein
       the at least one tab forms a portion of the annular wall of the bifurcated sheath hub;
       the at least one tab is joined with the bifurcated sheath hub via a structural hinge; and the at least one tab further comprises a tooth extending radially into the lumen; and the first coupler comprises a circumferential groove about the cannula portion;

wherein when the hemostasis device is coupled with the splittable sheath, the tooth is retained within the circumferential groove.

14. The delivery system of claim 4, wherein the bifurcated sheath hub further comprises an annular wall with an interior surface defining a lumen;

the first coupler comprises a nut retained about the cannula portion, wherein the nut further comprises a pair of ledges disposed on opposing sides of an outer surface of the nut;

the second coupler comprises a pair of clips joined with the bifurcated sheath hub, wherein each clip extends proximally and is positioned adjacent to one of the opposing lateral halves of the bifurcated sheath hub; and each clip defines a lip and a recess; and wherein when the hemostasis device is coupled with the splittable sheath, each ledge is retained within one of the recesses by one of the lips.

15. The delivery system of any of claims 9-14, wherein the hemostasis device further comprises an O-ring disposed about the cannula portion, the O-ring of slightly larger diameter than the interior surface of the annular wall of the bifurcated sheath hub, for creating a fluid-tight seal with the bifurcated sheath hub when the cannula portion is seated within the lumen.

16. The delivery system of any of claims 10-14, wherein the first connector comprises a first snap ring disposed about a distal end of the cannula portion, wherein the first snap ring is of slightly larger diameter than the interior surface of the annular wall of the sheath hub; and the second connector comprises a second snap ring formed on the interior surface of the annular wall, wherein the second snap ring is of slightly smaller diameter than the diameter of the interior surface of the annular wall adjacent the second snap ring; wherein the first snap ring is positioned distal and adjacent to the second snap ring when the hemostasis device is coupled with the splittable sheath; and the second snap ring disengages from the first snap ring when the opposing lateral halves of the bifurcated sheath hub are separated from each other to split the splittable sheath.

17. A delivery system for delivering a medical instrument intra-arterially or intravenously, the system comprising a hemostasis device having a cannula portion extending distally therefrom;

a first snap ring disposed on a distal end of the cannula portion; and a first engagement structure disposed on the cannula portion proximal to the first snap ring;

a splittable sheath;

a sheath hub connected with a proximal end of the splittable sheath, the sheath hub having an annular wall defining a lumen;

a second snap ring formed on an interior surface of the annular wall; and a second engagement structure disposed on a proximal end of the sheath hub;

a pair of handles connected with the sheath hub, each handle positioned on an opposing lateral side of the sheath hub;

wherein when the hemostasis device is connected with the splittable sheath, the cannula portion seats within the lumen of the sheath hub, the first snap ring engages the second snap ring, and the first engagement structure couples with the second engagement structure; and wherein by exerting an outward radial and distal force on the handles, the sheath hub and splittable sheath each separate longitudinally, the second engagement structure disengages from the first engagement structure, and the second snap ring disengages from the first snap ring.

18. The delivery system of claim 17, wherein when the hemostasis device is connected with the splittable sheath the first snap ring is positioned distal to the second snap ring.

19. The delivery system of claim 17, wherein the hemostasis device further comprises an O-ring disposed on the cannula portion for engagement with the interior surface of the annular wall of the sheath hub to create a fluid-tight seal between the hemostasis device and the sheath hub.

20. A delivery system for delivering a medical instrument intra-arterially or intravenously, the system comprising a hemostasis device having an outer surface;

a first coupling interface disposed circumferentially on a distal end of the outer surface; and an O-ring disposed circumferentially on the outer surface proximal to the first coupling interface;

wherein the outer surface of the hemostasis device defines an annular ledge proximal to the O-ring;

a sheath assembly predisposed in construction to longitudinally split into separate first and second halves, wherein an inner wall surface of the sheath assembly defines a generally cylindrical lumen, and the inner wall surface further defines a second coupling interface disposed circumferentially about the inner wall surface;

a first handle and a second handle each connected with an outer wall surface of the sheath assembly, the first handle positioned on the first half of the sheath assembly, the second handle positioned on the second half of the sheath assembly, and both the first and second handles positioned at a proximal end of the sheath assembly;

wherein the proximal end of the sheath assembly defines an annular rim;

wherein when the hemostasis device is connected with the sheath assembly, the first coupling interface engages the second coupling interface, and the O-ring frictionally engages the inner wall surface of the sheath assembly, and the annular ledge interfaces with the annular rim; and wherein by exerting an outward radial and distal force on each of the first and second handles, the sheath assembly separates longitudinally into the first and second halves, and the second coupling interface disengages from the first coupling interface.

21. A splittable sheath assembly for joining with a hemostasis device having a first snap ring and a first engagement structure, the splittable sheath assembly comprising a cannula predisposed to separate longitudinally;

a bifurcated sheath hub formed of opposing lateral halves joined with a proximal end of the cannula, the bifurcated sheath hub further having
an annular wall defining a lumen;
a second snap ring formed on an interior surface of the annular wall; and
a second engagement structure disposed on a proximal end of the sheath hub; and
a pair of handles connected with the bifurcated sheath hub, each handle positioned on an opposing lateral side of the bifurcated sheath hub;
wherein when the splittable sheath assembly is connected with the hemostasis device,
the second snap ring engages the first snap ring, and
the second engagement structure couples with the first engagement structure; and
wherein by exerting an outward radial and distal force on the handles,
the bifurcated sheath hub and cannula each separate longitudinally,
the second engagement structure disengages from the first engagement structure, and
the second snap ring disengages from the first snap ring.

* * * * *